(12) United States Patent
Hess et al.

(10) Patent No.: US 10,265,130 B2
(45) Date of Patent: Apr. 23, 2019

(54) SYSTEMS, DEVICES, AND METHODS FOR COUPLING END EFFECTORS TO SURGICAL DEVICES AND LOADING DEVICES

(71) Applicant: Ethicon Endo-Surgery, LLC, Guaynabo, PR (US)

(72) Inventors: Christopher J. Hess, Blue Ash, OH (US); Frederick E. Shelton, IV, Hillsboro, OH (US); Douglas E. Withers, Cincinnati, OH (US); Craig T. Gates, West Chester, OH (US); Jeffrey L. Savage, West Chester, OH (US); Adam D. Hensel, Cincinnati, OH (US); Monica L. Zeckel, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 292 days.

(21) Appl. No.: 14/966,330

(22) Filed: Dec. 11, 2015

(65) Prior Publication Data

US 2017/0165015 A1 Jun. 15, 2017

(51) Int. Cl.
*A61B 34/00* (2016.01)
*A61B 17/00* (2006.01)
*A61B 17/29* (2006.01)

(52) U.S. Cl.
CPC ........ *A61B 34/70* (2016.02); *A61B 17/00234* (2013.01); *A61B 17/29* (2013.01);
(Continued)

(58) Field of Classification Search
CPC ............ A61B 2017/2931; A61B 34/70; A61B 2017/2932; A61B 2017/00464;
(Continued)

(56) References Cited

U.S. PATENT DOCUMENTS 3,043,309 A 7/1962 McCarthy
3,358,676 A 12/1967 Frei et al.
(Continued)

FOREIGN PATENT DOCUMENTS

DE 101 49 421 A1 4/2003
DE 102010048516 A1 4/2012
(Continued)

OTHER PUBLICATIONS

International Search Report and Written Opinion for PCT Application No. PCT/US2016/065848 dated Mar. 31, 2017.
(Continued)

*Primary Examiner* — Todd J Scherbel
*Assistant Examiner* — Brooke Nicole Labranche
(74) *Attorney, Agent, or Firm* — Mintz Levin Cohn Ferris Glovsky and Popeo, P.C.

(57) ABSTRACT

Systems, devices, and methods designed to make it easier to couple end effectors to surgical instruments are provided. A variety of features are disclosed, which can be used independently or in conjunction with each other. The resulting benefits include enhanced visualization, more secure coupling, easier communication that coupling has occurred, self-clocking components with respect to each other, and more component modularity. In one exemplary embodiment, an end effector assembly having an end effector and an attachment arm includes a terminal end surface of the attachment arm having a three-dimensional configuration such that a portion of the end surface extends further away from a set location than another portion of the end surface extends from the location. In another exemplary embodiment, end effector assemblies include chambers having curved configurations that assist in self-clocking the assemblies with respect to surgical devices. Other features, devices, systems, and methods are also provided.

13 Claims, 22 Drawing Sheets

(52) U.S. Cl.
CPC .............. *A61B 2017/00464* (2013.01); *A61B 2017/00477* (2013.01); *A61B 2017/00862* (2013.01); *A61B 2017/2927* (2013.01); *A61B 2017/2931* (2013.01)

(58) Field of Classification Search
CPC .............. A61B 17/00234; A61B 17/29; A61B 17/320092; A61B 17/3201; A61B 18/1442; A61B 2017/00238; A61B 2017/00296; A61B 2017/00473; A61B 2017/00477; A61B 2018/1495
See application file for complete search history.

(56) References Cited

U.S. PATENT DOCUMENTS

| | | |
|---|---|---|
| 3,710,399 A | 1/1973 | Hurst |
| 3,893,448 A | 7/1975 | Brantigan |
| 3,906,217 A | 9/1975 | Lackore |
| 3,988,535 A | 10/1976 | Hickman et al. |
| 4,047,136 A | 9/1977 | Satto |
| 4,063,561 A | 12/1977 | McKenna |
| 4,099,192 A | 7/1978 | Aizawa et al. |
| 4,278,077 A | 7/1981 | Mizumoto |
| 4,384,584 A | 5/1983 | Chen |
| 4,585,282 A | 4/1986 | Bosley |
| 4,597,390 A | 7/1986 | Mulhollan et al. |
| 4,655,746 A | 4/1987 | Daniels et al. |
| 5,052,402 A | 10/1991 | Bencini et al. |
| 5,201,743 A | 4/1993 | Haber et al. |
| 5,282,806 A | 2/1994 | Haber et al. |
| 5,286,255 A | 2/1994 | Weber |
| 5,308,357 A | 5/1994 | Lichtman |
| 5,314,424 A | 5/1994 | Nicholas |
| 5,330,502 A | 7/1994 | Hassler et al. |
| 5,352,219 A | 10/1994 | Reddy |
| 5,392,917 A | 2/1995 | Alpern et al. |
| 5,407,293 A | 4/1995 | Crainich |
| 5,417,203 A | 5/1995 | Tovey et al. |
| 5,441,059 A | 8/1995 | Dannan |
| 5,468,250 A | 11/1995 | Paraschac et al. |
| 5,502,698 A | 3/1996 | Mochizuki |
| 5,507,297 A | 4/1996 | Slater et al. |
| 5,540,648 A | 7/1996 | Yoon |
| 5,562,655 A | 10/1996 | Mittelstadt et al. |
| 5,578,052 A | 11/1996 | Koros et al. |
| 5,593,402 A | 1/1997 | Patrick |
| 5,613,937 A | 3/1997 | Garrison et al. |
| 5,618,303 A | 4/1997 | Marlow et al. |
| 5,716,326 A | 2/1998 | Dannan |
| 5,762,255 A | 6/1998 | Chrisman et al. |
| 5,792,165 A | 8/1998 | Klieman et al. |
| 5,810,877 A | 9/1998 | Roth et al. |
| 5,881,615 A | 3/1999 | Dahl et al. |
| 5,928,263 A | 7/1999 | Hoogeboom |
| 5,980,455 A | 11/1999 | Daniel et al. |
| 6,024,748 A | 2/2000 | Manzo et al. |
| 6,059,719 A | 5/2000 | Yamamoto et al. |
| 6,099,537 A | 8/2000 | Sugai et al. |
| 6,159,200 A | 12/2000 | Verdura et al. |
| 6,309,397 B1 | 10/2001 | Julian et al. |
| 6,315,789 B1 | 11/2001 | Cragg |
| 6,419,688 B1 | 7/2002 | Bacher et al. |
| 6,471,172 B1 | 10/2002 | Lemke et al. |
| 6,589,211 B1 | 7/2003 | MacLeod |
| 6,595,984 B1 | 7/2003 | DeGuillebon |
| 6,626,824 B2 | 9/2003 | Ruegg et al. |
| 6,635,071 B2 | 10/2003 | Boche et al. |
| 6,723,043 B2 | 4/2004 | Kleeman et al. |
| 6,770,081 B1 | 8/2004 | Cooper et al. |
| 6,776,165 B2 | 8/2004 | Jin |
| 6,827,712 B2 | 12/2004 | Tovey et al. |
| 6,860,878 B2 | 3/2005 | Brock |
| 6,869,395 B2 | 3/2005 | Page et al. |
| 6,884,213 B2 | 4/2005 | Raz et al. |
| 6,936,003 B2 | 8/2005 | Iddan |
| 6,942,674 B2 | 9/2005 | Belef et al. |
| 6,986,738 B2 | 1/2006 | Glukhovsky et al. |
| 6,994,708 B2 | 2/2006 | Manzo |
| 7,039,453 B2 | 5/2006 | Mullick et al. |
| 7,042,184 B2 | 5/2006 | Oleynikov et al. |
| 7,066,879 B2 | 6/2006 | Fowler et al. |
| 7,083,579 B2 | 8/2006 | Yokoi et al. |
| 7,122,028 B2 | 10/2006 | Looper et al. |
| 7,125,403 B2 | 10/2006 | Julian et al. |
| 7,169,104 B2 | 1/2007 | Ueda et al. |
| 7,199,545 B2 | 4/2007 | Oleynikov et al. |
| 7,211,094 B2 | 5/2007 | Gannoe et al. |
| 7,241,290 B2 | 7/2007 | Doyle et al. |
| 7,297,142 B2 | 11/2007 | Brock |
| 7,331,967 B2 | 2/2008 | Lee et al. |
| 7,429,259 B2 | 9/2008 | Cadeddu et al. |
| 7,448,993 B2 | 11/2008 | Yokoi et al. |
| 7,559,887 B2 | 7/2009 | Dannan |
| 7,566,331 B2 | 7/2009 | Looper et al. |
| 7,604,642 B2 | 10/2009 | Brock |
| 7,651,471 B2 | 1/2010 | Yokoi et al. |
| 7,666,181 B2 | 2/2010 | Abou El Kheir |
| 7,678,043 B2 | 3/2010 | Gilad |
| 7,691,103 B2 | 4/2010 | Fernandez et al. |
| 7,691,126 B2 | 4/2010 | Bacher |
| 7,699,835 B2 | 4/2010 | Lee et al. |
| 7,722,599 B2 | 5/2010 | Julian et al. |
| 7,862,553 B2 | 1/2011 | Ewaschuk |
| 7,894,882 B2 | 2/2011 | Mullick et al. |
| 7,901,398 B2 | 3/2011 | Stanczak et al. |
| 8,021,358 B2 | 9/2011 | Doyle et al. |
| 8,038,612 B2 | 10/2011 | Paz |
| 8,052,636 B2 | 11/2011 | Moll et al. |
| 8,057,502 B2 | 11/2011 | Maliglowka et al. |
| 8,088,062 B2 | 1/2012 | Zwolinski |
| 8,128,643 B2 | 3/2012 | Aranyi et al. |
| 8,182,414 B2 | 5/2012 | Handa et al. |
| 8,187,166 B2 | 5/2012 | Kuth et al. |
| 8,377,044 B2 | 2/2013 | Coe et al. |
| 8,397,335 B2 | 3/2013 | Gordin et al. |
| 8,398,544 B2 | 3/2013 | Altamirano |
| 8,409,076 B2 | 4/2013 | Pang et al. |
| 8,475,361 B2 | 7/2013 | Barlow et al. |
| 8,518,024 B2 | 8/2013 | Williams et al. |
| 8,623,011 B2 | 1/2014 | Spivey |
| 8,636,648 B2 | 1/2014 | Gazdzinski |
| 8,721,539 B2 | 5/2014 | Shohat et al. |
| 8,764,735 B2 | 7/2014 | Coe et al. |
| 8,845,661 B2 | 9/2014 | D'Arcangelo et al. |
| 9,142,527 B2 | 9/2015 | Lee et al. |
| 9,282,879 B2 | 3/2016 | Farin et al. |
| 9,308,011 B2 | 4/2016 | Chao et al. |
| 9,408,628 B2 | 8/2016 | Altamirano |
| 9,451,937 B2 | 9/2016 | Parihar |
| 2001/0051766 A1 | 12/2001 | Gazdzinski |
| 2003/0060702 A1 | 3/2003 | Kuth et al. |
| 2003/0114731 A1 | 6/2003 | Cadeddu et al. |
| 2004/0093039 A1 | 5/2004 | Schumert |
| 2004/0133235 A1 | 7/2004 | Bacher |
| 2004/0152941 A1 | 8/2004 | Asmus et al. |
| 2005/0033354 A1 | 2/2005 | Montalvo et al. |
| 2005/0085697 A1 | 4/2005 | Yokoi et al. |
| 2005/0119640 A1 | 6/2005 | Sverduk et al. |
| 2005/0131396 A1 | 6/2005 | Stanczak et al. |
| 2005/0165449 A1 | 7/2005 | Cadeddu et al. |
| 2005/0215983 A1 | 9/2005 | Brock |
| 2005/0250984 A1 | 11/2005 | Lam et al. |
| 2005/0272972 A1 | 12/2005 | Iddan |
| 2005/0272974 A1 | 12/2005 | Iddan |
| 2005/0273139 A1 | 12/2005 | Krauss et al. |
| 2005/0288555 A1 | 12/2005 | Binmoeller |
| 2006/0079933 A1 | 4/2006 | Hushka et al. |
| 2006/0149135 A1 | 7/2006 | Paz |
| 2006/0184161 A1 | 8/2006 | Maahs et al. |
| 2006/0190035 A1 | 8/2006 | Hushka et al. |
| 2006/0195015 A1 | 8/2006 | Mullick et al. |
| 2006/0229592 A1 | 10/2006 | Yokoi et al. |
| 2006/0258905 A1 | 11/2006 | Kaji et al. |

(56) References Cited

U.S. PATENT DOCUMENTS

| | | |
|---|---|---|
| 2007/0010709 A1 | 1/2007 | Reinschke |
| 2007/0049966 A1 | 3/2007 | Bonadio et al. |
| 2007/0073247 A1 | 3/2007 | Ewaschuk |
| 2007/0093792 A1 | 4/2007 | Julian et al. |
| 2007/0123748 A1 | 5/2007 | Meglan |
| 2007/0156015 A1 | 7/2007 | Gilad |
| 2007/0255100 A1 | 11/2007 | Barlow et al. |
| 2007/0255273 A1 | 11/2007 | Fernandez et al. |
| 2007/0270651 A1 | 11/2007 | Gilad et al. |
| 2007/0299387 A1 | 12/2007 | Williams et al. |
| 2008/0015413 A1 | 1/2008 | Barlow et al. |
| 2008/0015552 A1 | 1/2008 | Doyle et al. |
| 2008/0045003 A1 | 2/2008 | Lee et al. |
| 2008/0140090 A1 | 6/2008 | Aranyi et al. |
| 2008/0142005 A1 | 6/2008 | Schnell |
| 2008/0154299 A1 | 6/2008 | Livneh |
| 2008/0242939 A1 | 10/2008 | Johnston |
| 2008/0243106 A1 | 10/2008 | Coe et al. |
| 2008/0287926 A1 | 11/2008 | Abou El Kheir |
| 2008/0312499 A1 | 12/2008 | Handa et al. |
| 2009/0005636 A1 | 1/2009 | Pang et al. |
| 2009/0005638 A1 | 1/2009 | Zwolinski |
| 2009/0209947 A1 | 8/2009 | Gordin et al. |
| 2010/0249700 A1 | 9/2010 | Spivey |
| 2011/0040322 A1 | 2/2011 | Major |
| 2011/0087265 A1 | 4/2011 | Nobis et al. |
| 2011/0087266 A1* | 4/2011 | Conlon .................. A61B 17/29 606/205 |
| 2011/0087267 A1 | 4/2011 | Spivey et al. |
| 2011/0115891 A1 | 5/2011 | Trusty |
| 2011/0208007 A1 | 8/2011 | Shohat et al. |
| 2011/0230869 A1 | 9/2011 | Altamirano |
| 2011/0288560 A1 | 11/2011 | Shohat et al. |
| 2012/0053402 A1 | 3/2012 | Conlon et al. |
| 2012/0053406 A1 | 3/2012 | Conlon et al. |
| 2012/0065627 A1 | 3/2012 | Ghabrial et al. |
| 2012/0078290 A1 | 3/2012 | Nobis et al. |
| 2012/0078291 A1 | 3/2012 | Nobis et al. |
| 2012/0083826 A1 | 4/2012 | Chao et al. |
| 2012/0088965 A1 | 4/2012 | Stokes et al. |
| 2012/0089093 A1 | 4/2012 | Trusty |
| 2012/0095298 A1 | 4/2012 | Stefanchik et al. |
| 2012/0259325 A1 | 10/2012 | Houser et al. |
| 2012/0316575 A1 | 12/2012 | Farin et al. |
| 2013/0085341 A1 | 4/2013 | Nobis et al. |
| 2013/0138091 A1 | 5/2013 | Coe et al. |
| 2013/0138129 A1* | 5/2013 | Garrison ............ A61B 18/1445 606/170 |
| 2014/0005474 A1 | 1/2014 | Farin et al. |
| 2014/0066711 A1 | 3/2014 | Farin et al. |
| 2014/0088569 A1 | 3/2014 | Parihar et al. |
| 2014/0088637 A1* | 3/2014 | Parihar .................. A61B 17/29 606/205 |
| 2014/0088638 A1 | 3/2014 | Parihar |
| 2014/0243799 A1 | 8/2014 | Parihar |
| 2014/0243800 A1 | 8/2014 | Parihar |
| 2014/0277018 A1 | 9/2014 | Parihar |
| 2014/0378953 A1 | 12/2014 | Coe et al. |
| 2015/0088191 A1 | 3/2015 | Coe et al. |
| 2017/0055970 A1 | 3/2017 | Hess et al. |
| 2017/0055971 A1 | 3/2017 | Hess et al. |

FOREIGN PATENT DOCUMENTS

| | | |
|---|---|---|
| EP | 1 709 900 A1 | 10/2006 |
| JP | 2005-261734 A | 9/2005 |
| JP | 2008-518716 A | 6/2008 |
| WO | 2008/015666 A2 | 2/2008 |
| WO | 2010/060436 A1 | 6/2010 |
| WO | 2010/081482 A1 | 7/2010 |
| WO | 2010/111319 A1 | 9/2010 |
| WO | 2010/114634 A1 | 10/2010 |
| WO | 2011/044353 A1 | 4/2011 |
| WO | 2011/081702 A1 | 7/2011 |
| WO | 2011/089565 A1 | 7/2011 |
| WO | 2012/035524 A2 | 3/2012 |
| WO | 2012/040183 A1 | 3/2012 |
| WO | 2012/112622 A2 | 8/2012 |
| WO | 2012/126967 A2 | 9/2012 |
| WO | 2013/007764 A2 | 1/2013 |
| WO | 2013/048963 A2 | 4/2013 |
| WO | 2014/052177 A1 | 4/2014 |

OTHER PUBLICATIONS

International Search Report dated Mar. 21, 2011; International Application No. PCT/US2010/051812 (7 pages).
International Preliminary Report dated Apr. 19, 2012; International Application No. PCT/US2010/051812; (10 pages).
International Search Report dated Mar. 2, 2012; International Application No. PCT/US2011/050198 (7 pages).
International Preliminary Report dated Mar. 14, 2013; International Application No. PCT/US2011/050198 (10 pages).
International Search Report dated Dec. 12, 2011; International Application No. PCT/US2011/052327 (5 pages).
International Preliminary Report dated Apr. 4, 2013; International Application No. PCT/US2011/052327 (9 pages).
International Search Report dated Apr. 3, 2013; International Application No. PCT/US2012/056900 (3 pages).
International Preliminary Report dated Apr. 10, 2014; International Application No. PCT/US2012/056900 (8 pages).
International Search Report dated Dec. 20, 2013; International Application No. PCT/US2013/060803 (3 pages).
International Preliminary Report dated Apr. 9, 2015; International Application No. PCT/US2013/060803 (9 pages).
International Search Report dated May 28, 2014; International Application No. PCT/US2014/015738 (4 pages).
International Preliminary Report on Patentability dated Sep. 11, 2015; International Application No. PCT/US2014/015738 (12 pages).
US Application as filed on Oct. 9, 2009 for U.S. Appl. No. 12/576,529 (18 pages).

* cited by examiner

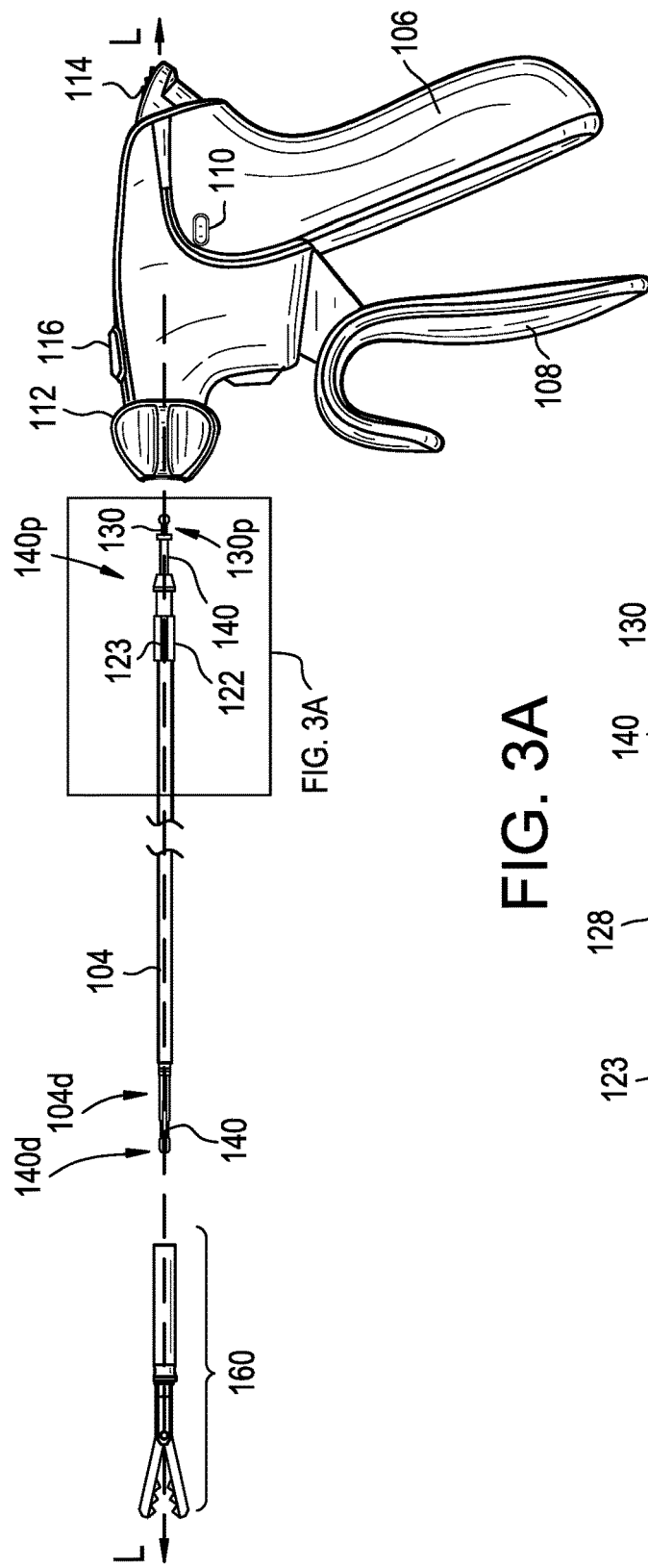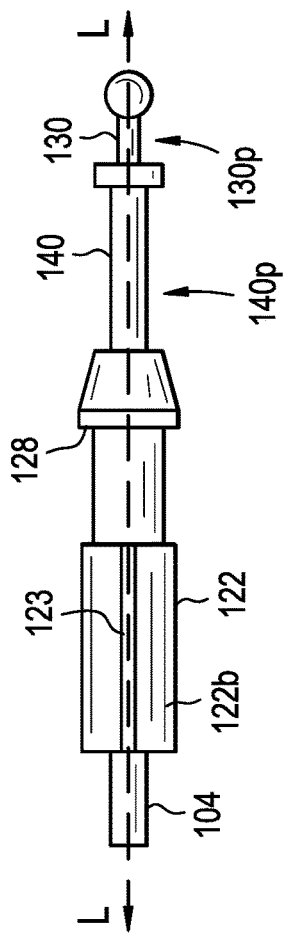

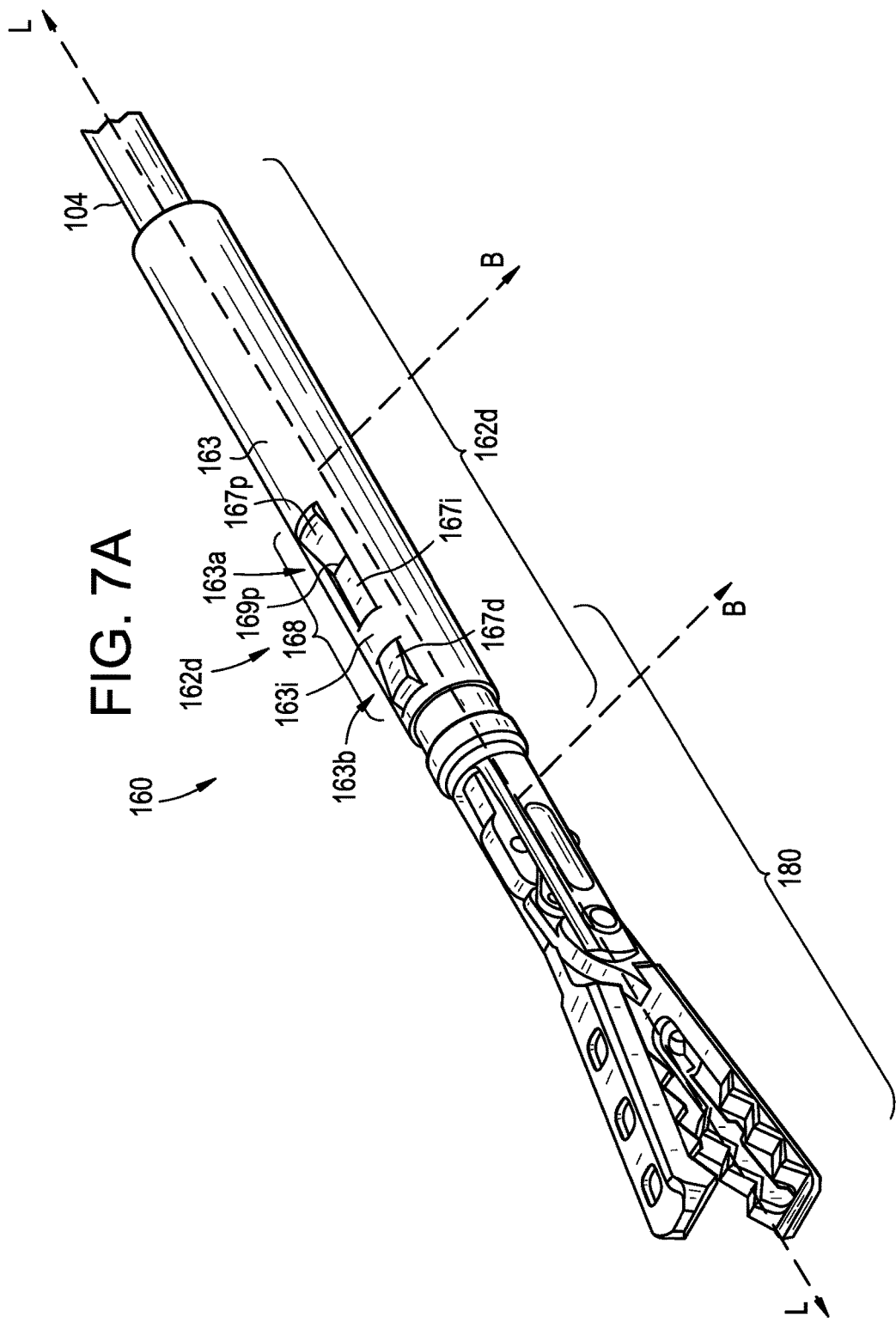

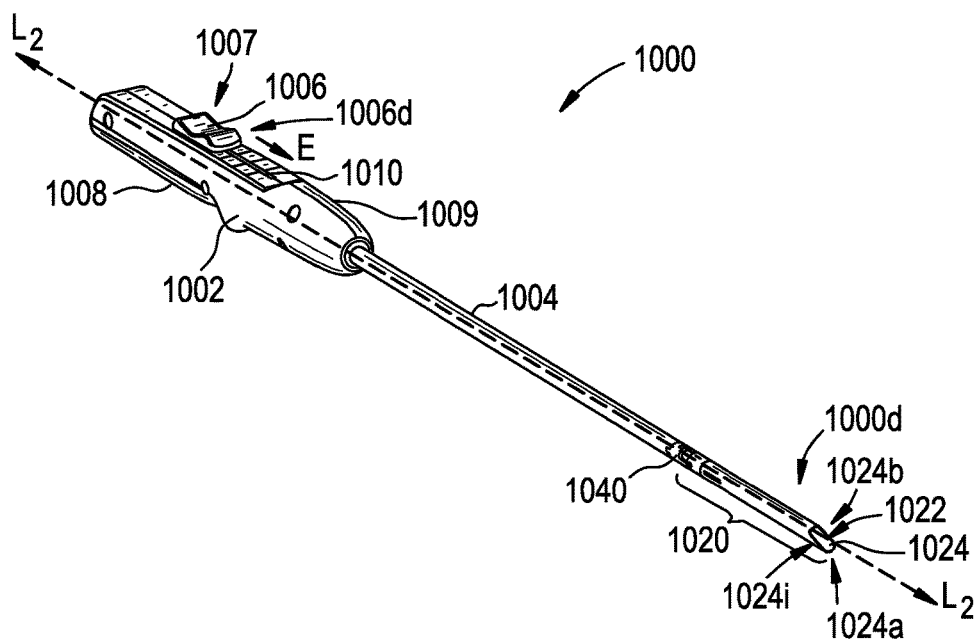
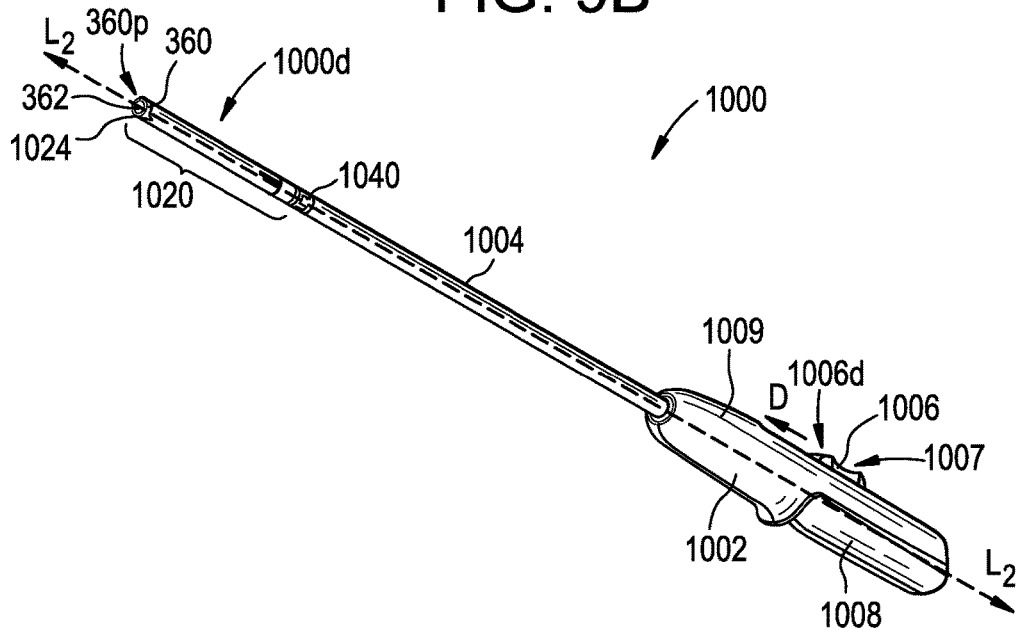

SYSTEMS, DEVICES, AND METHODS FOR COUPLING END EFFECTORS TO SURGICAL DEVICES AND LOADING DEVICES

FIELD

The present disclosure relates to systems, devices, and methods for attaching an end effector to a surgical device, and more particularly provides for improved configurations that make it easier to connect an end effector to a surgical device in vivo.

BACKGROUND

Minimally invasive surgical techniques such as endoscopies and laparoscopies are often preferred over traditional open surgeries because the recovery time, pain, and surgery-related complications are typically less with minimally invasive surgical techniques. In many laparoscopic procedures, the abdominal cavity is insufflated with carbon dioxide gas. The abdominal wall is pierced and a cannula or trocar is inserted into the abdominal cavity. Surgeons can then perform a variety of surgical procedures while minimizing patient trauma.

Many procedures require a variety of different functions be performed at the surgical site. These functions can be performed by different instruments, each being tailored to perform a particular function. Alternatively, a single instrument having interchangeable and replaceable end effectors can be used, with each end effector being tailored to perform a particular function. Often, multiple instruments or end effectors are disposed or used at a surgical site at the same time, and/or during the same procedure, and multiple surgical access ports can be used to accommodate the instruments. The instruments used by a surgeon can include an end effector that is designed to perform a particular function at the surgical site, a handle to operate the end effector from outside of a subject, and a shaft connecting the handle and end effector. The diameter of the end effector is usually substantially larger than the shaft, and thus techniques have been developed that allow end effectors to be introduced through a single, larger port via an instrument, sometimes referred to as a loading device or loader.

While systems that provide for a surgical device to be introduced to a surgical site through a first port and a loader to be introduced to the surgical site through a second port so that the loader can present and/or assist in coupling the end effector to the device are known, such systems and devices are limited in their capabilities. For example, while the ability to use different end effectors with a single instrument provides some flexibility and versatility, there is still a need for additional flexibility and versatility in other components of the system, such as for different types of surgeries and different types of anatomies. In some instances, end effectors need to be associated with particular instrument configurations in order to operate properly (e.g., specific shaft configurations extending between a handle portion and the end effector). Another deficiency of some existing instruments is that the modular end effector head freely rotates when a surgeon places a twist load on the device, thereby limiting the control a surgeon has over operation of the end effector.

Still further, coupling an end effector to a surgical instrument or device in vivo can be difficult to do because it can be difficult to manipulate a shaft of the instrument and the end effector to easily attach with one another. While visualization techniques, such as using an endoscope or the like at the surgical site, can aid a surgeon during the attachment process, additional instrumentation can take up much needed real estate. Viewing devices can also be difficult to maneuver to get a good view of the surgical site and relevant instrumentation, tissue, organs, etc. Still further, the view of the viewing device can become blurry, for instance due to being obstructed by objects in the body and/or having fluid, tissue fragments, or other materials deposited on the lens. In some instances, the lack of good vision in vivo can cause the surgical device, e.g., a shaft of the device, to become bent due to the device being directed to locations to which it should not be directed. Further, sometimes a surgeon may think an attachment has been made, only to later discover that no attachment occurred. This can lead to the end effector falling off the device, or the device being inoperable due to the end effector being improperly loaded.

It is desirable for systems, devices, and methods used in minimally invasive surgeries to have further flexibility and versatility. It is further desirable for such systems, devices, and methods to allow a modular end effector to more easily be aligned so that the end effector can easily and securely connect to a surgical device that will be used to operate the end effector. It is also desirable for a surgeon to be notified when a secure attachment has been established between the end effector and the surgical device that will be used to operate the end effector and/or know when the end effector has been removed from the surgical device. It is still further desirable for notification and ease-of-coupling features of this nature to be incorporated into a loading device that presents end effectors to surgical instruments in vivo such that a surgeon can know when an end effector has been properly loaded or unloaded from the loading device.

SUMMARY

A variety of systems, devices, and methods are provided that enhance the often tedious step of coupling an end effector to a surgical instrument and/or coupling an end effector to a loading device used in the delivery of an end effector to a surgical instrument. These systems, devices, and methods provide a variety of benefits, including enhanced visualization, more secure coupling between two components and certainty that two coupled components are securely fastened together, improved abilities to self-clock or self-align one component with respect to another as they two components are coupled together, and more modularity between surgical device components. The enhancements provided for herein are described across at least one, and sometimes more than one, of the illustrated embodiments, and claims associated herewith generally incorporate some portion of the enhancements described. As discussed, however, the enhancements provided for can be mixed and matched as appropriate to provide for many different configurations of loading devices, surgical devices, and end effector assemblies.

In one exemplary embodiment, a surgical device includes an end effector assembly having both an end effector and at attachment arm. The end effector can be disposed at a first end, while the attachment arm can be disposed at a second, opposite end. The attachment arm includes a terminal end surface that defines an opening for receiving a surgical instrument that is configured to be coupled to the end effector assembly. The terminal end surface has a first portion that extends further away from the first end along a longitudinal axis of the end effector assembly than a second portion of the terminal end surface extends away from the first end along the longitudinal axis of the end effector assembly. This three-dimensional configuration of the terminal end surface can be helpful in identifying a location and/or an orientation of the end effector assembly with respect to the surgical instrument and/or with respect to a loading device for delivering the end effector assembly to the surgical instrument.

In some embodiments, the attachment arm can include an elongate shaft that extends between the terminal end surface and the end effector, with the end effector being operatively coupled to an end of the elongate shaft that is opposed to the terminal end surface. The terminal end surface can have a troughed, scallop shape in which a width of a first portion and a width of a second portion can be greater than a width of an intermediate portion disposed between the first and second portions. In some embodiments, the width of the first and second portions can be substantially the same, while in other embodiments these two widths can also be different. The attachment arm can include an elastic conical end sleeve. As part of the sleeve, a flexible outer skirt can extend from the terminal end surface. The end effector can be any variety of end effectors, including but not limited to a jaw assembly.

The device can also include other components with which the end effector assembly can be used. For example, the device (or sometimes referred to as a system) can include an end effector loader that has a distal chamber for disposing the end effector assembly in it. A distal end of the end effector loader can include an opening that provides access to the distal chamber, which can be used, for example, to allow a surgical instrument to pass through it to engage and couple the end effector assembly to the instrument. The opening can be defined by a distal-most outer wall (sometimes referred to herein as a terminal end) in which a first portion of the wall extends further away from a proximal end of the end effector loader along a longitudinal axis of the end effector loader than a second portion of the wall extends away from the same proximal end. In some embodiments, an orientation of the terminal end surface of the attachment arm can be configured to substantially mirror an orientation of the distal-most outer wall of the end effector loader. Thus, the terminal end surface can likewise have a first portion that extends further away from an end effector along a longitudinal axis of the end effector assembly than a second portion of the terminal end surface extends away from the same portion of the end effector.

In another exemplary embodiment, an end effector assembly includes an end effector disposed at a first end and a receiving sleeve disposed at a second, opposite end. The receiving sleeve can include a chamber formed at a terminal end of the second, opposite end that is furthest from the first end of the end effector assembly. The chamber can include one or more coupling features formed on an inner surface of the chamber. More particularly, the inner surface can have a curved configuration that is capable of directing one or more coupling features that are complementary to the coupling features formed on the inner surface of the chamber towards the coupling feature(s) of the chamber. More specifically, the curved configuration is such that the complementary coupling feature(s) of a surgical instrument that is advanced into the chamber, towards the first end of the end effector assembly, is directed towards the coupling feature(s) formed on the inner surface of the chamber.

In some embodiments, the coupling feature(s) of the chamber includes opposed slots that are configured to receive complementary opposed splines of a surgical instrument. The inner surface of the chamber can include opposed first and second apexes that are disposed approximately 90 degrees around a circumference of the chamber from the opposed slots. Portions of the inner surface that extend from the apexes form a funnel towards the opposed slots such that the end effector assembly is configured to rotate with respect to a shaft of a surgical instrument that is advanced into the chamber. As a result, complementary opposed splines that are part of the shaft of the surgical instrument being advanced into the chamber move towards the opposed slots of the chamber.

Further, an outer surface of the end effector assembly can have one or more coupling features formed on it, which can be used, for example, to couple the end effector assembly to a loading device that is used in conjunction with coupling the end effector assembly to a surgical instrument. The coupling feature(s) of the outer surface can be configured to couple with one or more complementary coupling features of the loading device. While the end effector assembly is coupled to the loading device, the end effector assembly can be coupled to a surgical instrument, for example, by engaging the coupling feature(s) of the chamber of the receiving sleeve with complementary coupling feature(s) of the surgical instrument. The coupling feature(s) of the outer surface can include opposed channels having a width at a first end of the channel that is greater than a width at a second end of the channel, with the first end being disposed at a terminal end of the end effector assembly.

One exemplary embodiment of a surgical method can include advancing a shaft of a surgical instrument towards a loading device having an end effector assembly associated with it. A distal end of the shaft can be contacted with a terminal end surface of an attachment end of the end effector assembly to identify a position of the end effector assembly. The terminal end surface can include a first portion that extends further away from an end effector end of the end effector assembly along a longitudinal axis of the end effector assembly than a second portion of the terminal end surface extends away from the same end effector end. This terminal end surface configuration promotes identification of the position of the end effector assembly at least because of the three-dimensional aspect of it. The shaft of the surgical instrument can be coupled to the end effector assembly to enable an actuator associated with the shaft to operate an end effector located at the end effector end of the end effector assembly.

In some embodiments, the terminal end surface of the end effector assembly can be part of a flexible, three-dimensional attachment arm of the end effector assembly. Further, in some embodiments, the terminal end surface can include a troughed, scallop shape in which a width of the first portion and a width of the second portion is greater than a width of an intermediate portion disposed between the first and second portions. The widths of the first and second portions can be substantially similar, or they can be different.

The method can include advancing the end effector assembly out of the loading device to expose the terminal end surface of the end effector assembly to an environment outside of the loading device. Further, a shape of the terminal end surface of the end effector assembly can be substantially similar to a shape of a distal-most outer wall of the loading device that defines an opening through which the end effector assembly passes when it is advanced out of the loading device. In some embodiments, coupling the shaft to the end effector assembly can include advancing the shaft of the surgical instrument into the attachment end of the end effector assembly. In such embodiments, a configuration of an inner surface that defines an opening of the attachment end is configured to cause the end effector assembly to rotate into a position in which one or more coupling features of the attachment end of the end effector assembly engage one or more coupling features of the distal end of the shaft to couple the shaft to the end effector assembly.

BRIEF DESCRIPTION OF DRAWINGS

This disclosure will be more fully understood from the following detailed description taken in conjunction with the accompanying drawings, in which:

FIG. 2 is a side view of the surgical device of FIG. 1A, the device being partially disassembled to illustrate modular inner, intermediate, and outer shafts that are removably and replaceably coupled to a housing of the device and the end effector assembly being removably and replaceably coupled to the outer shaft;

FIG. 3A is a detailed side view of a proximal end of the inner, intermediate, and outer shafts of FIG. 2, as well as a hub with which they are associated;

FIG. 7A is a perspective view of the end effector assembly of FIG. 1A;

FIG. 9A is a perspective view of the loading device of FIG. 8;

FIG. 9B is a further perspective view of the loading device of FIG. 9A;

DETAILED DESCRIPTION

Figure 1A:
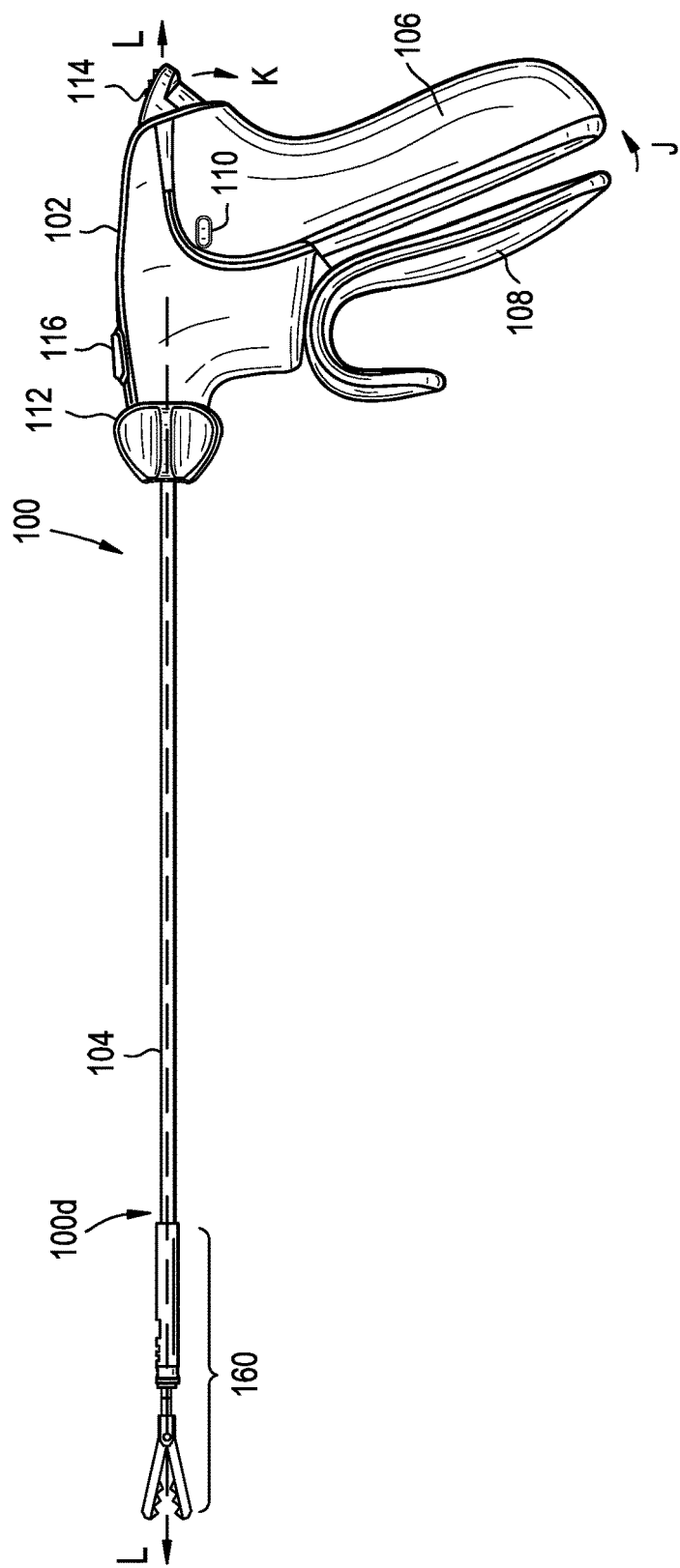
FIG. 1A is a side view of one exemplary embodiment of a surgical device having an end effector assembly coupled to a distal end of the device.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention. Further, in the present disclosure, like-numbered components of the various embodiments generally have similar features when those components are of a similar nature and/or serve a similar purpose. Additionally, to the extent features, sides, or directions are described herein as being a "first feature" or "first direction" or a "second feature" or "second direction," such numerical ordering is generally arbitrary, and thus such numbering can be interchangeable.

The terms "proximal" and "distal" are used herein with reference to a clinician manipulating the handle portion of the surgical instrument. The term "proximal" referring to the portion closest to the clinician and the term "distal" referring to the portion located away from the clinician. However, in instances when multiple instruments or devices are being operated simultaneously, e.g., a surgical instrument and a loading device as provided for below, use of the terms proximal and distal can be used in other contexts, depending on the point of view. It will be further appreciated that, for convenience and clarity, spatial terms such as "vertical," "horizontal," "up," and "down" may be used herein with respect to the drawings. However, surgical instruments are used in many orientations and positions, and these terms are not intended to be limiting and/or absolute. Additionally, to the extent terms for applying a force to a component are described as involving "pushing" or "pulling," a person skilled in the art will recognize that actions such as pushing or pulling can typically be performed interchangeably without departing from the spirit of the present disclosure. Still further, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

The present disclosure generally relates to a surgical system that makes it easier to attach an end effector to a shaft of surgical device or instrument that is configured to operate the end effector. A variety of different features are provided in this context across a number of embodiments, as are other features that generally make using surgical devices easier, efficient, and/or more effective. The resulting benefits of the features provided for herein include surgical devices that are less likely to become damaged due to improper use or failure in making the appropriate connection between the end effector and the surgical instrument, and fewer failures using the device in general. The features provided for in the present disclosures also improve the ability for more components of surgical devices and systems to be cleaned and reused, and allow for more modularity, increases in cost savings, and decreases in surgical waste.

As described in greater detail below, some of the features provided for are part of an end effector assembly that includes the end effector to be used at the surgical site. It is noted that some skilled in the art may refer to an end effector assembly as an end effector, although in the present disclosure the end effector is typically identified as a portion of an end effector assembly. Other features provided for are on the loading device that presents the end effector to be attached to the surgical instrument, while still other features are provided for on one or more shafts of the surgical instrument to complement features of the end effector assembly or to create their own stand-alone beneficial functions. Some of the described features that improve the modularity and usability of the present disclosure include: modular shafts (e.g., FIGS. 2-6B), locking springs for holding an end effector assembly in a "ready-to-load" configuration and capable of indicating to a user when the end effector assembly is ready to be loaded and actually loaded (e.g., FIGS. 7A-7C), self-aligning features that help align an end effector assembly in a loading device and/or align an end effector assembly to a surgical instrument (e.g., FIGS. 11A-13C), chambers on the end effector assembly designed to self-clock or self-align the end effector assembly with respect to a surgical instrument and/or a loading device (e.g., FIGS. 14-18B), and a delivery chamber (e.g., FIGS. 8-11B, 14, and 20) and an end effector assembly (e.g., FIGS. 19 and 20) having a terminal end with a three-dimensional configuration in which a portion of the terminal end is more distal from a handle of the loading device than another portion of the terminal end, making it easier to seat or couple the end effector assembly to the surgical instrument.

Figure 1B:
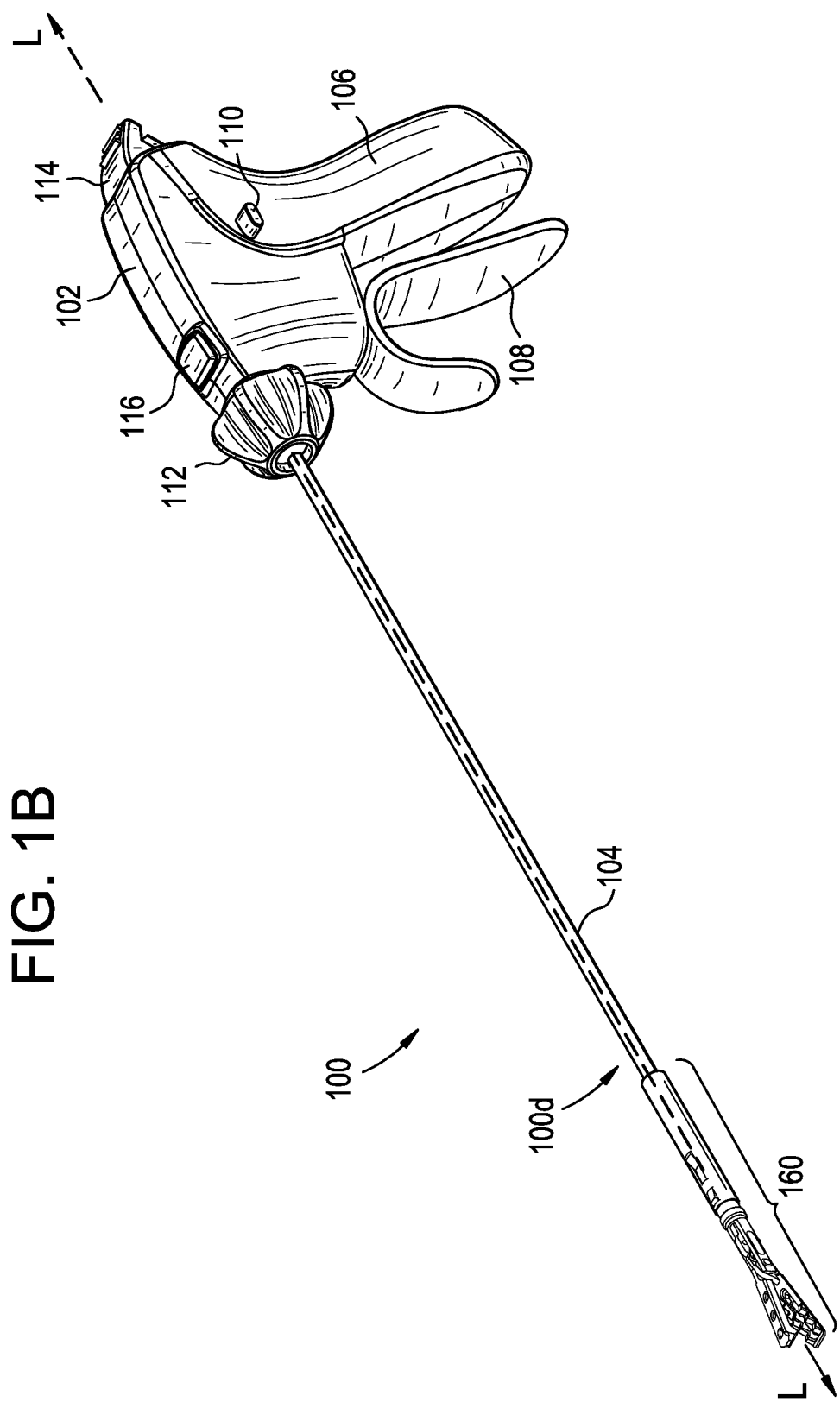
FIG. 1B is a perspective view of the surgical device and end effector assembly of FIG. 1A.
Figure 8:
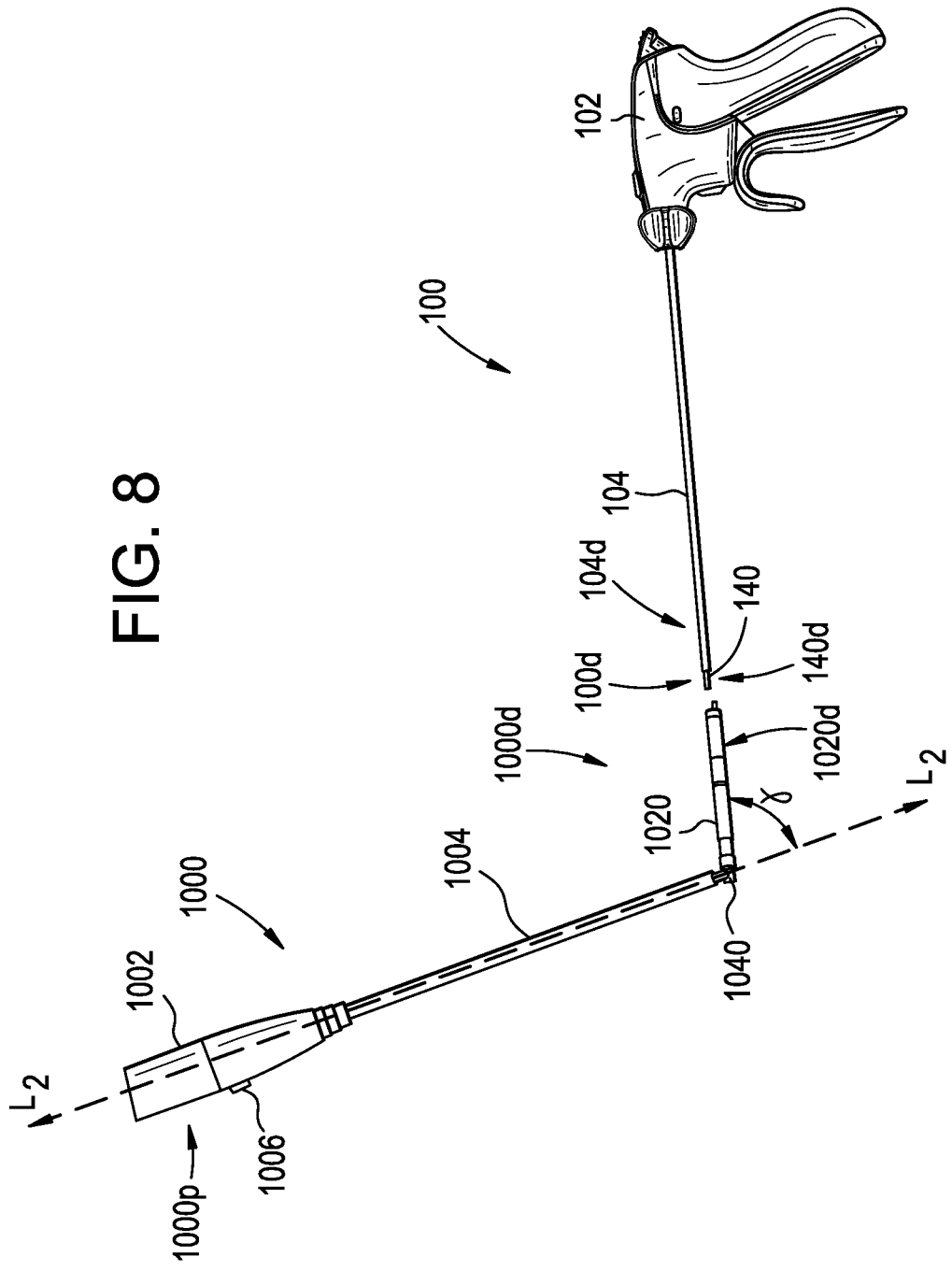
FIG. 8 is a perspective view of the surgical device of FIG. 1A being used in conjunction with an exemplary embodiment of a loading device prior to loading an end effector assembly associated with the loading device onto the surgical device.

FIGS. 1A and 1B show an exemplary surgical instrument or device 100 having an end effector assembly 160 attached to its distal end 100d that can be used to perform a variety of actions during a surgical procedure, depending, at least in part, on the type of end effector provided for as part of the assembly. As described herein, the end effector assembly 160 can be provided for at a surgical site by way of a loading device 1000 passed through a separate opening than the surgical instrument 100, as shown in FIG. 8, and then the end effector assembly 160 can be coupled to the surgical instrument 100 and removed from the loading device 1000 for use at the surgical site. Examples of loading devices are described later herein at least with respect to FIGS. 9A-11B, 13A-14, 18A, 18B, and 20, and as otherwise known to those skilled in the art.

As shown, the device 100 has a housing or handle portion 102 and an outer elongate shaft 104 extending distally from the housing 102, the shaft 104 being configured to have an end effector assembly selectively coupled to it. The elongate shaft 104 can extend from a distal, upper portion of the housing 102, along a central longitudinal axis L of the shaft 104 extending therethrough, and it can be removably and replaceably attached to operable components in the housing 102 as described herein. The housing 102 can include a stationary arm 106 and a actuator 108, such as a pivotable trigger, that is configured to move relative to the housing 102 to actuate an end effector when an end effector is coupled to the shaft 104. As shown, the actuator 108 can be coupled to a distal portion of the housing 102, and when the end effector is any of the jaw assemblies provided for in the present disclosure, or jaw assemblies otherwise derivable therefrom, the actuator 108 can be operated to open and close the jaws. A person skilled in the art will understand that while the present disclosure primarily illustrates and discusses using the actuator 108 to open and close jaws, the actuator 108 can be configured to control a wide variety of end effectors, and thus perform a variety of functions, based, at least in part, on the end effector and related assembly that is associated with the device, the surgical procedure with which the device is being used, and the preferences of the surgeon.

The internal actuation components that can be used to translate motion of the actuator 108 to movement of jaws can have many different configurations, including being mechanically, electrically, and/or optically-based, and components of this nature are known to those skilled in the art, thus exact details about every such component is unnecessary. Some non-limiting examples of such components are discussed in greater detail in U.S. application Ser. No. 14/836,069, filed on Aug. 26, 2015, and entitled "Surgical Device having Actuator Biasing and Locking Features," which is hereby incorporated by reference in its entirety. In general, such components can be disposed in, or attached to, portions of the housing 102 and/or the shaft 104. Some exemplary, non-limiting examples of these components include but are not limited to motors, controllers, and levers. Other implementations that can be used to actuate the jaws include but are not limited to actuators, gears, levers, triggers, and sliders. Further, a person skilled in the art will recognize other functions that the actuator 106, or other means of actuation, can perform without departing from the spirit of the present disclosure.

Still further, some non-limiting examples of features that can be incorporated as part of the device 100 include a locking switch 110 to selectively lock the actuator 108 in a fixed angular position relative to the housing, a knob 112 configured to rotate the elongate shaft 104, and thus an end effector assembly 160 coupled thereto, a locking member 114 configured to advance an inner shaft 130 (proximal end illustrated in FIGS. 2 and 3A-3E and a distal end illustrated in FIGS. 4A-4C, 6A, and 6B) distally and proximally along a longitudinal axis L of the shaft 104, and a release button 116 that can be used to de-couple components of the device 100 from other components (e.g., inner and intermediate shafts 130, 140 from the housing 102), as described in greater detail below and in U.S. application Ser. No. 14/836, 069, filed on Aug. 26, 2015, and entitled "Surgical Device having Actuator Biasing and Locking Features," the contents of which is incorporated by reference in its entirety above. As explained below, movement of the inner shaft 130, as well as an intermediate shaft 140 (proximal end illustrated in FIGS. 2 and 3A-3E and a distal end illustrated in FIGS. 2, 4A-4C, 6A, and 6B), can help couple and de-couple an end effector assembly such as the end effector assembly 160 from a distal end 104d of the elongate shaft 104, as well as to operate the end effector associated with the end effector assembly 160 via the actuator 108 when the end effector assembly 160 is coupled to the device 100.

Turning more specifically to the outer shaft 104, as well as inner and intermediate shafts 130, 140 that can be used in conjunction with the same to attach an end effector assembly to the outer shaft 104 and/or to actuate an end effector of the end effector assembly, each of the three shafts 104, 130, 140 can be generally elongate, cylindrical, and concentric such that they share the central longitudinal axis L. Proximal ends 104p, 130p, 140p of one or more of the shafts 104, 130, 140 can have modularity features that enable the respective shaft to be disassociated from the housing 102. As a result, differently sized and configured shafts can be used with different types of end effectors and end effector assemblies (e.g., jaws, suturing devices, 3 millimeter vs. 5 millimeter devices), different types of surgical procedures (e.g., bariatric, tissue repair, general purpose, etc.), and/or different types of patients (e.g., pediatric as compared to adults). Additionally, each of the three shafts 104, 130, 140 can be modular with respect to each other, and with respect to the device 100 as a whole, e.g., with respect to the housing 102 and end effector assemblies.

As shown in FIGS. 2, 3A-3C, 3E, and 3F, a proximal end 104p of the outer shaft 104 can be disposed within a hub 122, which itself can be configured to be removed from and re-coupled to the housing 102. The proximal end 104p sits within a distal portion 124d of a lumen 124 of the hub 122 such that the outer shaft 104 terminates within the hub 122. The distal portion 124d of the lumen 124 can have a diameter sized to be complementary to a diameter of the proximal end 104p of the outer shaft 104 such that outer shaft 104 can be press-fit into the distal portion 124d. In some embodiments, an opening 118 can be provided in the proximal portion 104p of the outer shaft 104 to help align or otherwise secure a location of the outer shaft 104 with respect to the hub 122, and thus the housing 102. This is accomplished, by way of non-limiting example, by the opening 118 engaging a complementary post (not shown) of the hub 122 such that the outer shaft 104 does not rotate independently of the hub 122. Further, the length of the opening 118 can be such that an amount of axial travel (proximal-distal) by the outer shaft 104 is restricted by ends of the opening 118 engaging said complementary post. A person skilled in the art will recognize other alignment features that can also be used, and thus the outer shaft 104 is not limited to using the opening 118, or openings in general, for alignment. Further, in some embodiments the hub 122 can include features for mating with the rotating knob 112 such that rotation of the knob 112 causes the hub, and the shafts 104, 130, 140 associated therewith, to rotate. In the illustrated embodiment opposed keys 123 formed on an outer surface of the hub 122 can be configured to mate with complementary grooves formed in an inner wall of the rotating knob 112.

Figure 3B:
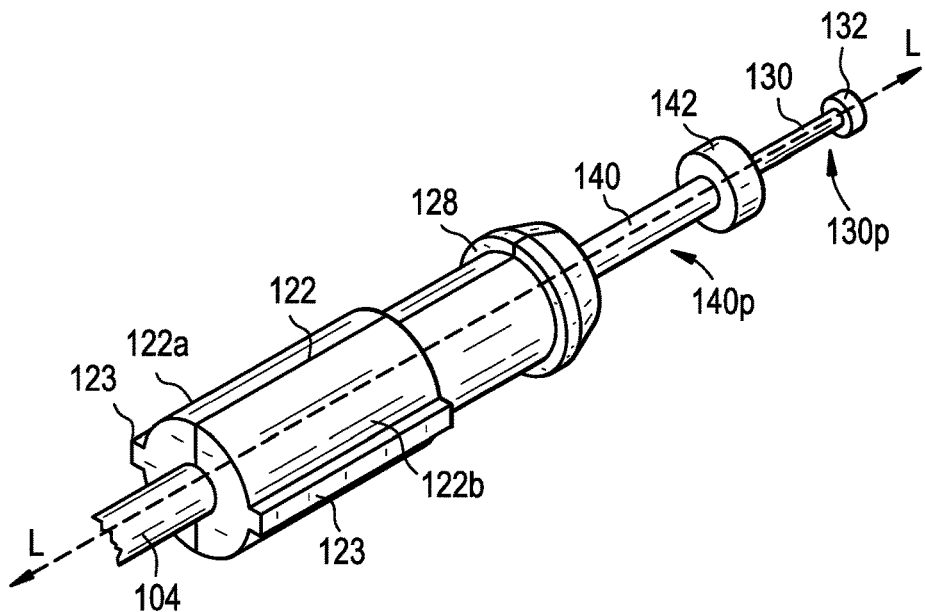
FIG. 3B is a detailed perspective view of the proximal end of the inner, intermediate, and outer shafts, as well as the hub, of FIG. 3A.
Figure 3D:
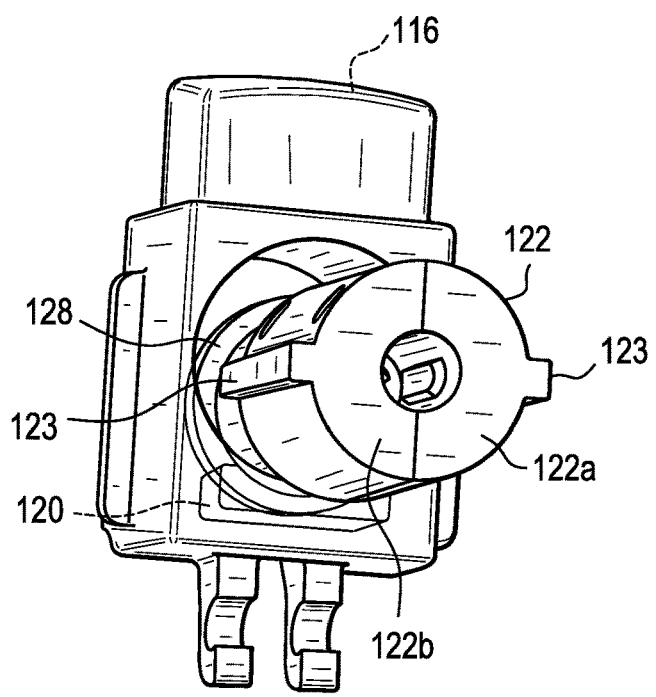
FIG. 3D is a perspective, partially transparent view of the hub of FIG. 3B and a release button associated with the housing of FIG. 3C.
Figure 3C:
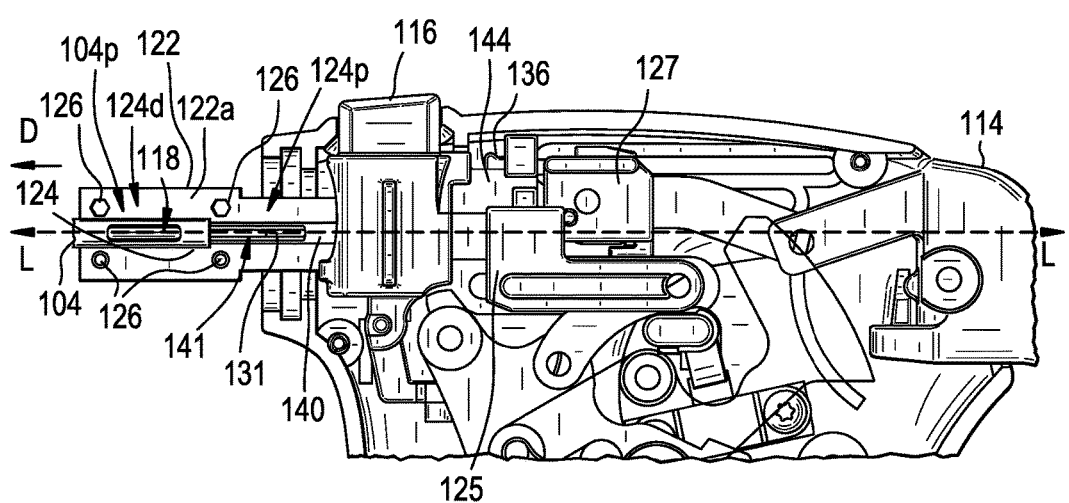
FIG. 3C is a side view of the housing and the inner, intermediate, and outer shafts of FIG. 2, with a portion of the housing and a portion of the hub of FIG. 3A hidden from view.
Figure 3E:
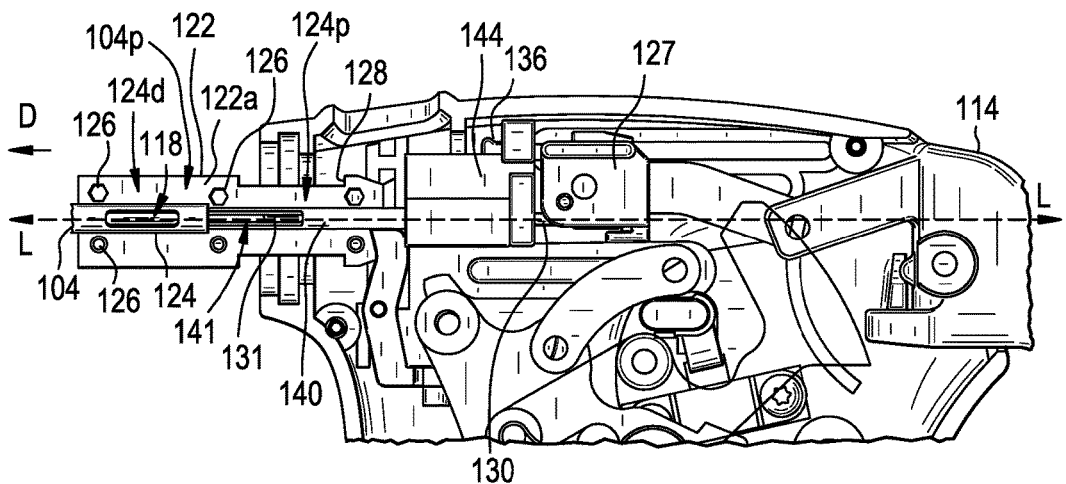
FIG. 3E is the side view of the housing and the inner, intermediate, and outer shafts of FIG. 3C with the release button of FIG. 3D and an intermediate shaft sled of the housing hidden from view.

The outer shaft 104 can be modular with respect to the hub 122 using a number of different configurations. In the illustrated embodiment, the hub 122 is configured to be separated into two pieces 122a, 122b by disconnecting male and/or female mating features associated with one piece 122a of the hub 122 from complementary female and/or male mating features associated with the other piece 122b of the hub 122, both the male and female mating features being represented by features 126 in FIGS. 3C, 3E, and 3F. A person skilled in the art will recognize other configurations that can allow the outer shaft 104 to be separated from the hub 122, including but not limited to by applying enough force in a distal direction D to disengage the outer shaft 104 from the hub 122. Likewise, the hub 122 can be modular with respect to the housing 102 using a number of different configurations. As shown in FIG. 3D, the hub 122 includes a proximal ledge 128 configured to engage a complementary ledge 120 formed as part of the release button 116. The housing 102 is configured such that when the release button 116 is in its default position, i.e., it is not depressed, the complementary ledges 128, 120 engage each other and the hub 122 is coupled to the housing 102; when the release button 116 is depressed towards the housing 102, the ledge 120 of the release button 116 is advanced downwards, thereby disengaging from the ledge 128 of the hub 122. When the ledges 128, 120 are disengaged, the hub 122 can be de-coupled from the housing 102, for instance by pulling it distally away from the housing 102, and subsequently separated into the two pieces 122a, 122b to remove the outer shaft 104 from the hub 122.

The hub 122 can also be configured to receive the intermediate and the inner shafts 140, 130. As shown, a proximal portion 124p of the lumen 124 has a diameter sized to be complementary to the diameter of the intermediate shaft 140. Unlike the outer shaft 104, which terminates at a location within the hub 122, the intermediate shaft 140, as well as the inner shaft 130 disposed therein, extends proximally beyond the hub 122, into the housing 102. As shown in FIG. 3B, each of the intermediate and inner shafts 140, 130 includes flanges 142, 132 formed at proximal ends 140p, 130p thereof, which are used to selectively engage internal actuation components of the housing 102. The translating movement of the intermediate and inner shafts 140, 130 can be controlled by the internal actuation components, which themselves can be controlled by features of the housing 102 that are accessible to a user, e.g., the actuator 108 and the locking member 114. For example, an intermediate shaft sled 125 (shown in FIG. 3C) can be operated by the actuator 108 to advance and retract a sliding coupler 144 to which the intermediate shaft 140 is coupled, and an inner shaft sled 127 (shown in FIGS. 3C and 3E, and transparent in FIG. 3F) can be operated by the locking member 114 to advance and retract a receiver 134 to which the inner shaft 130 is coupled.

Figure 3F:
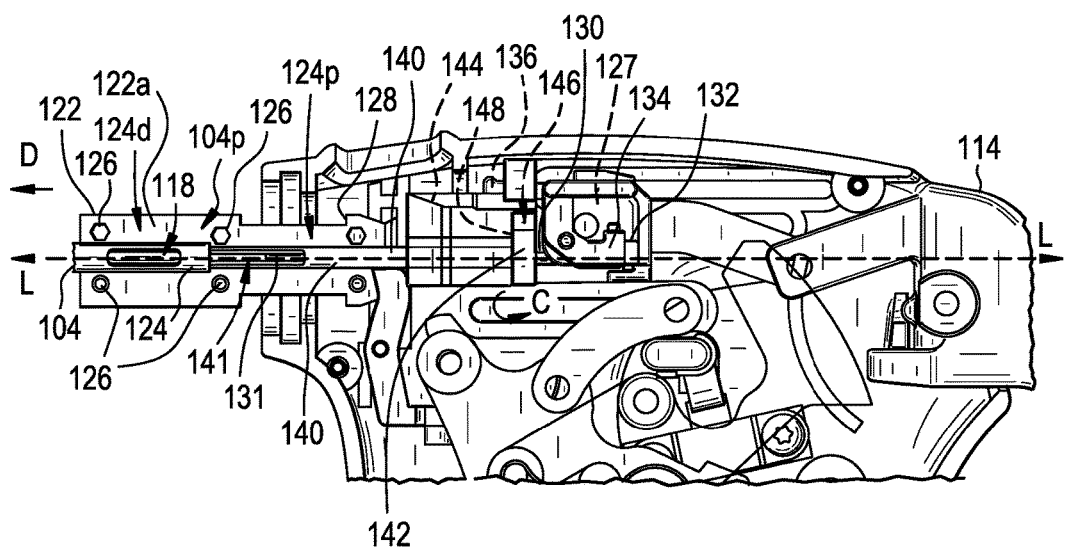
FIG. 3F is the side view of the housing and the inner, intermediate, and outer shafts of FIG. 3D with a sliding coupler and an inner shaft sled of the housing illustrated as being transparent.

The internal actuation components can be manipulated, for instance by pressing the release button 116, to disengage the flanges 142, 132 from internal actuation components, thereby allowing the intermediate and inner shafts 140, 130 to be de-coupled from the housing. More particularly, in the illustrated embodiment, the flange 142 of the intermediate shaft 140 is coupled to the sliding coupler 144. As shown in FIG. 3F, the flange 142 sits within a coupling chamber 146 of the sliding coupler 144. However, when the release button 116 is depressed towards the housing 102, it causes the sliding coupler 144 to rotate in a counter-clockwise direction C, which in turn causes a lip 148 adjacent to the coupling chamber 146 to rise up such that the lip 148 is no longer is in contact with the flange 142. As a result, the flange 142 can be removed from the coupling chamber 146 and the intermediate shaft 140 disassociated from the housing 102.

Likewise, the flange 132 of the inner shaft 130 can be engaged by the receiver 134 (FIG. 3F) associated with an extension arm 136 that is mated to the sliding coupler 144. When the release button 116 is depressed towards the housing 102 and causes the sliding coupler 144 to rotate in the counter-clockwise direction C, this causes the receiver 134 to be raised such that it is no longer in contact with the flange 132. As a result, the flange 132 can be disassociated from the receiver 134 and the inner shaft 130 disassociated from the housing 102.

When any of the outer, intermediate, and inner shafts 104, 140, 130 are disassociated from the housing 102, they can be cleaned, modified, or have any other desirable action performed to them. For example, upon removal, each of the shafts can be cleaned, sterilized, and re-attached to the housing 102, or to a housing of another surgical device. The modular nature of the shafts 104, 140, 130 allows for their easy adaptability for different sizes, procedures, etc., and makes it easier to clean them. Additionally, the modular nature of the shafts 104, 140, 130 makes it easier to repair, clean, sterilize, and/or modify the components of the housing 102, including the internal actuation components. Thus, not only are the shafts 104, 140, 130 more reusable, but so is the housing 102 and its related components.

In some embodiments, alignment features can be provided as part of any or all of the shafts 104, 140, 130 to secure or at least restrict a location of the shafts with respect to the housing 102 and/or each other. One such alignment feature, the opening 118 of the outer shaft 104, is discussed above. By way of further non-limiting example, an opening 141 is provided in a proximal portion 140p of the intermediate shaft 140 and helps align or otherwise secure a location of the intermediate shaft 140 with respect to the housing 102 and/or the outer shaft 104. The opening 141 engages a complementary post (not shown) of the hub 122 and/or the outer shaft 104 such that the intermediate shaft 140 does not rotate independently of the hub 122 or the outer shaft 104. Further, the length of the opening 141 is such that an amount of axial travel (proximal-distal) by the intermediate shaft 140 is restricted by the ends of the opening 141 engaging said complementary post. A person skilled in the art will recognize other alignment features that can be also be used, and thus the intermediate shaft 140 is not limited to using the opening 141, or openings in general, for alignment.

By way of a non-limiting example for the inner shaft 130, opposed channels 131 can extend a portion of a length of the inner shaft 130 to help align or otherwise secure a location of the inner shaft 130 with respect to the housing 102. The channels 131 engage one or more complementary protrusions (not shown) formed in any of the intermediate shaft 140, the outer shaft 104, the hub 122, or another component of the housing 102. As a result, the inner shaft 130 does not rotate independently of one or more of the intermediate shaft 140, the outer shaft 104, and the hub 122. A person skilled in the art will recognize other alignment features and configurations that can also be used, and thus the inner shaft 130 is not limited to using channels 131, or channels in general, for alignment.

Figure 4A:
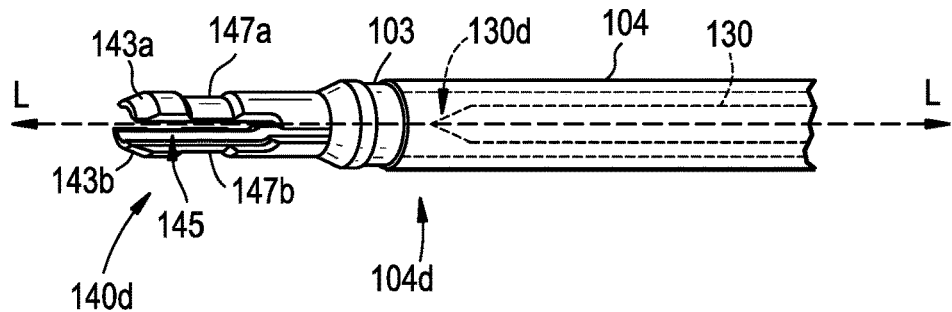
FIG. 4A is a side view of a distal end of the inner, intermediate, and outer shafts of FIG. 2.
Figure 4B:
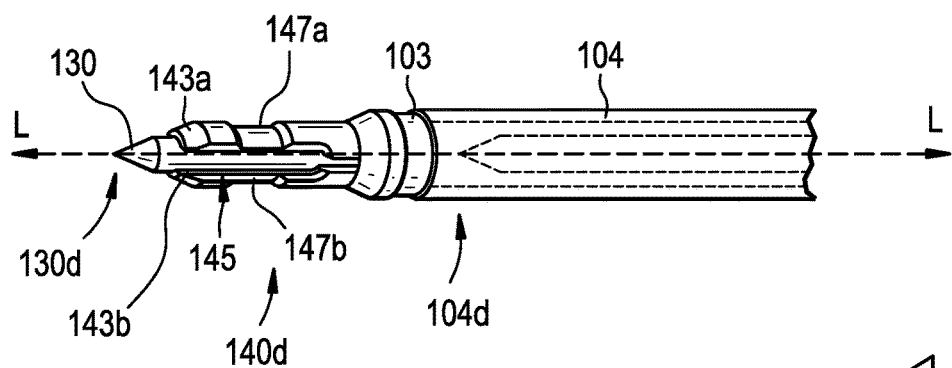
FIG. 4B is a side view of the distal end of the intermediate and outer shafts of FIG. 4A having the inner shaft of FIG. 4A disposed therein such that a distal end of the inner shaft extends distally beyond the distal ends of the intermediate and outer shafts.

The distal ends 104d, 140d, 130d of the outer, intermediate, and inner shafts 104, 140, 130 can be operated together to couple an end effector assembly to the distal end 104d of the outer shaft 104. FIGS. 4A and 4B illustrate the distal end of the shaft in greater detail, including exemplary attachment mechanisms located at the distal end of the elongate shaft so that an end effector assembly (not shown in FIGS. 4A and 4B) can be mated to the shaft 104. While the attachment mechanism can vary, in the illustrated embodiment a circumferential groove 103 can be positioned around an outer surface of a distal portion 104d of the shaft 104. First and second arms 143a, 143b can project distally from the distal end 104d of the outer shaft 104 and can be coupled to or otherwise integrally formed on the intermediate shaft 140. The arms 143a, 143b can be axially slidable relative the outer shaft 104, for instance to actuate an end effector coupled to the outer shaft 104, and can be resiliently deflectable medially into an elongate opening or gap 145. The arms 143a, 143b can each have a mating feature(s), which in this embodiment are stepped lateral notches 147a, 147b. The elongate or gap formed between the arms 143a, 143b can also provide additional access for purposes of cleaning, sterilizing, and otherwise preparing the intermediate shaft 140 for being reused.

Figure 4C:
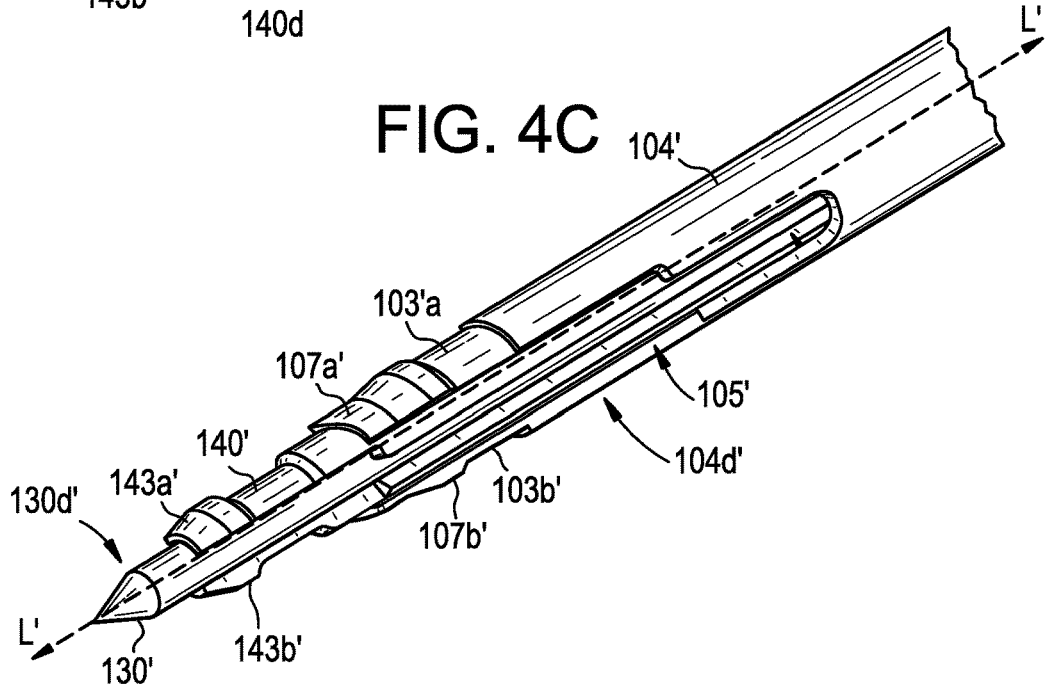
FIG. 4C is a perspective view of an alternative exemplary embodiment of a distal end of an outer shaft used in conjunction with the inner and intermediate shafts of FIG. 4B.

An elongate opening or gap 105' can likewise be formed in a distal end 104d' of an outer shaft 104', as shown in an alternative embodiment in FIG. 4C, to provide additional features to enhance reusability of the outer shaft 104'. As shown, the shaft 104' includes deflectable arms 107a', 107b' that deflect in a manner similar to the arms 143a, 143b and can include a mating feature like stepped lateral notches 103a', 103b'. The alternative embodiment in FIG. 4C also provides for an intermediate shaft 140' similar to the intermediate shaft 140, as well as an inner shaft 130' similar to the inner shaft 130. More details about the inner shafts 130, 130' are provided below.

A distal tip 130d, 130d' of the inner shaft 130, 130' can be positioned medially relative to the arms 143a, 143b and 143a', 143b', and can be axially slidable relative to the arms 143a, 143b and 143a', 143b'. More specifically, the distal tip 130d, 130d' can slide between an unlocked position in which the distal tip 130d, 130d' is proximal to the arms 143a, 143b and 143a', 143b', allowing medial deflection of the arms 143a, 143b and 143a', 143b' (as shown in FIG. 4A), and a locked position in which the distal tip 130d, 130d' is aligned with or distal to the arms 143a, 143b and 143a', 143b', and to prevent medial deflection of the arms 143a, 143b and 143a', 143b' (as shown in FIGS. 4B and 4C). In certain aspects, the inner shaft 130, 130' and the arms 143a, 143b and 143a', 143b' can slide independently along the longitudinal axis L, L' of the elongate shaft 104, 104'. The distal tip 130d, 130d' of the inner shaft 130, 130' can also be referred to herein as an obturator tip that can be pointed and/or sharpened such that the distal tip 130d, 130d' can pierce through tissue. In the illustrated embodiments, the distal ends of the arms 143a, 143b and 143a', 143b', and the distal end 104d of the outer shaft 104 and/or the distal ends of the arms 107a', 107b', can taper from a proximal-to-distal direction. The taper can facilitate passing the arms 143a, 143b and 143a', 143b' and the outer shaft 104 and/or the distal ends of the arms 107a', 107b' through an incision (not shown), such as an incision formed by the distal tip 130d, 130d'. As will be appreciated by persons skilled in the art, the distal tip 130d, 130d' of the inner shaft 130, 130' need not be sharpened or pointed and the outer and intermediate shafts 104, 140 can include various types of attachment mechanisms for mating with an end effector assembly and need not include a taper, grooves, etc.

Figure 5:
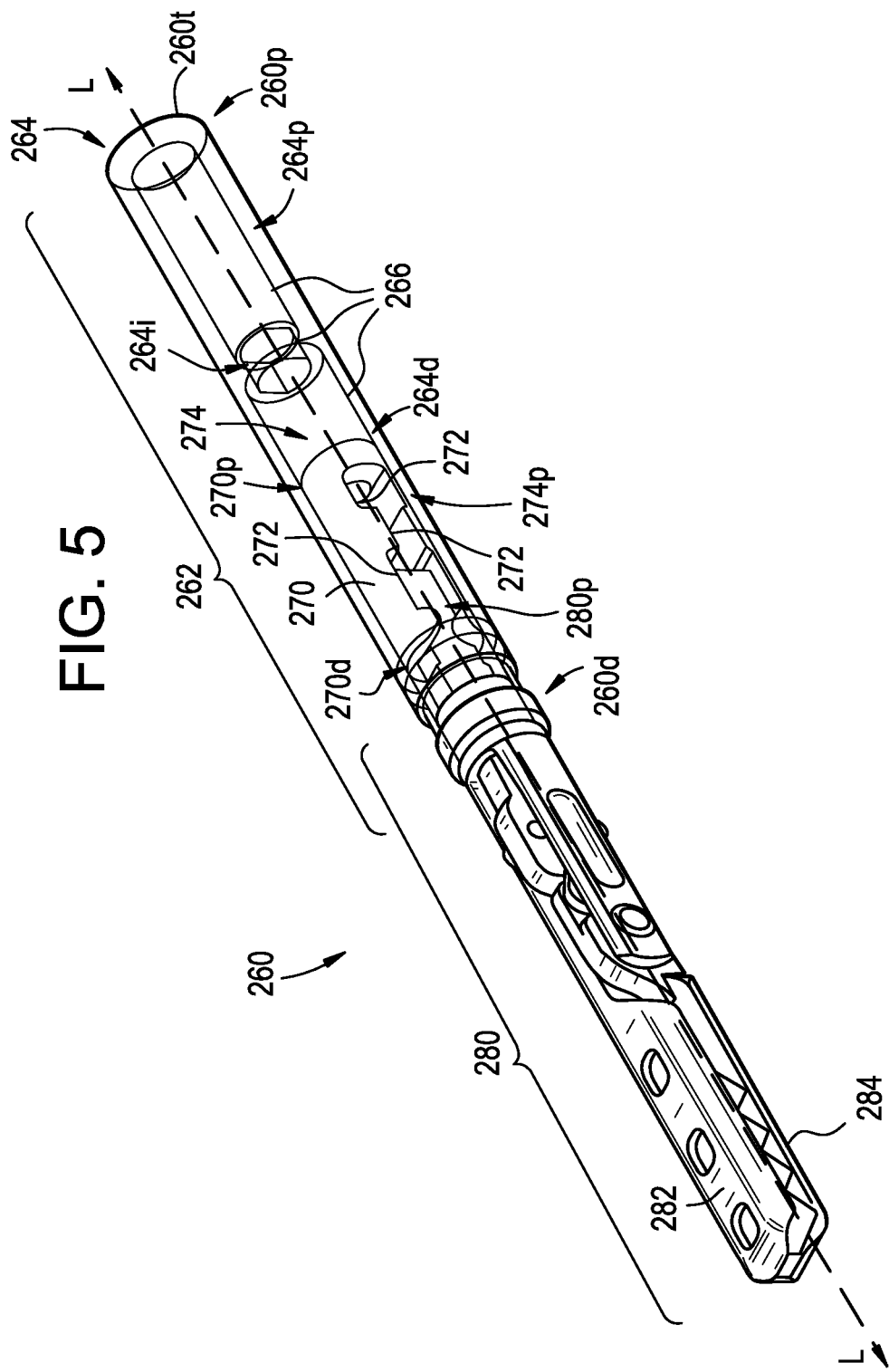
FIG. 5 is a perspective view of one exemplary embodiment of an end effector assembly for use in conjunction with the surgical device of FIG. 1A.

One non-limiting example of an end effector assembly 260 configured to be removably and replaceably coupled to the distal end 104d of the outer shaft 104 is illustrated in FIG. 5. As shown, the end effector assembly 260 includes an attachment arm or receiving sleeve 262, an end effector receiver or coupler 270 at least partially disposed within the attachment arm 262, and an end effector 280. The attachment arm 262 can be a shaft that extends between a terminal end 260t of the end effector assembly 260 and a portion of the end effector 280. As shown, the attachment arm is generally cylindrical in shape and is designed to help facilitate removable and replaceable connections with surgical instruments (e.g., the outer shaft 104 of the instrument 100) and end effectors (e.g., the end effector 280).

A lumen 264 is disposed across the length of the attachment arm 262 from the assembly's attachment end or proximal end 260p to its end effector coupling end or distal end 260d, with the lumen 264 being defined by an inner sidewall 266. The lumen 264 has multiple diameters and a non-uniform shape and/or size across its length. In the illustrated embodiment, a proximal portion 264p of the lumen 264 includes a diameter configured to receive the outer shaft 104, an intermediate portion 264i of the lumen 264 includes a diameter that is smaller than a diameter of the outer shaft 104 such that the outer shaft 104 does not extend therethrough, and a distal portion 264d of the lumen 264 includes a diameter that is configured to have the end effector receiver or coupler 270 disposed therein. The proximal portion 264p can also include one or more mating features to engage complementary mating features of the outer shaft 104 to couple the two together, such as mating features 267' shown in FIGS. 6A and 6B as ribs and described in greater detail below.

The end effector receiver or coupler 270 has a geometry at its proximal end 270p that is complementary in shape to the geometry of the distal end 140d of the intermediate shaft 140. As a result, when the inner shaft 130 expands the arms 143a, 143b of the intermediate shaft 140, the arms 143a, 143b form an interference fit with the complementary shape of inner walls 272 of the coupler 270 that define a proximal portion 274p of a lumen 274 formed therein. A distal end 270d of the coupler 270 can be configured to receive the end effector 280, e.g., the jaw assembly having jaws 282 and 284 illustrated in FIG. 5, and a shape of the inner walls 272 that define a distal portion 274d of the lumen 274 can be complementary to the shape of a proximal end 280p of the end effector 280. As shown, while the attachment arm 262 extends between the terminal end 260t and the end effector 280, a portion of the end effector 280 can be disposed within the attachment arm 262 by virtue of being disposed in the coupler 270.

Figure 6A:
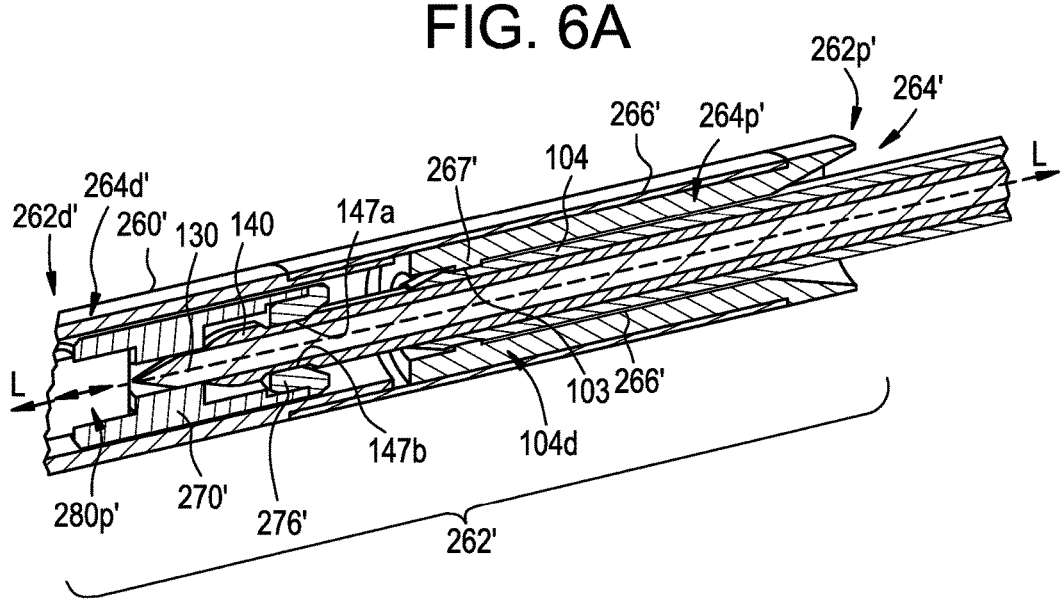
FIG. 6A is a perspective, detailed, cross-sectional view of another exemplary embodiment of an end effector assembly, the end effector assembly having disposed therein the inner, intermediate, and outer shafts of FIG. 2, with the end effector assembly being coupled to the outer shaft.
Figure 6B:
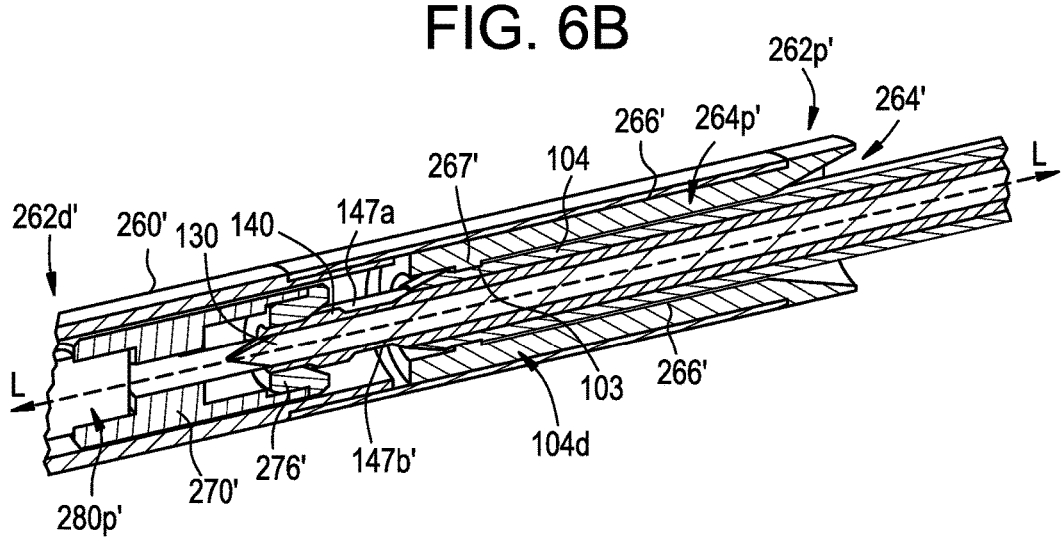
FIG. 6B is the perspective, detailed, cross-sectional view of the end effector assembly and the inner, intermediate, and outer shafts of FIG. 6A, with the end effector assembly being in a pushed-off configuration.

FIGS. 6A and 6B illustrate an exemplary interaction between an end effector assembly 260' and the intermediate and inner shafts 140, 130. As shown, the end effector assembly 260' includes an attachment arm or receiving sleeve 262', an end effector receiver or coupler 270' at least partially disposed within the attachment arm 262', and an end effector 280', of which a proximal end 280p' is illustrated. The distal end 104d of the outer shaft 104 can extend into a proximal portion 264p' of a lumen 264' that extends from a proximal end 262p' to a distal end 262d' of the attachment arm 262'. In the illustrated embodiment, the circumferential groove 103 formed in the shaft 104 can mate with one or more mating features 267', as shown ribs, formed on an inner sidewall 266' of the attachment arm 262' to prevent relative axial motion between the outer shaft 104 and the end effector assembly 260' when they are coupled together for use.

Likewise, the stepped lateral notches 147a, 147b of the intermediate shaft 140 can mate to a ring 276' associated with the coupler 270', with the coupler 270' being disposed in a distal portion 264d' of the lumen 264', thus preventing relative axial motion. The ring 276' can be rigidly and fixedly connected to the proximal end 280p' of the end effector 280' via the coupler 270', with the proximal end 280p' being adapted to actuate jaws (not shown). More particularly, axial movement of the intermediate shaft 140 will cause axial movement of the jaw actuator 280p' relative to the housing 102, thereby causing jaws of the end effector 280' to open and close. For example, an actuator 108 can be advanced towards a stationary arm 106, as illustrated in FIG. 1A with the arrow J, to distally advance the intermediate shaft 140, and the locking member 114 can be rotated towards the housing 102, as illustrated in FIG. 1A with the arrow K, to distally advance the inner shaft 130. FIG. 6B illustrates the end effector assembly 260' ready to be detached from the elongate shaft 104, i.e., in a pushed-off configuration. In particular, distally advancing the intermediate shaft 140 can push the ring 276' distally until the ribs 267' unseat from the circumferential groove 103 and allows the distal end 104d of the elongate shaft 104 to be removed from the end effector assembly 260'.

A person skilled in the art will recognize that the surgical device 100 illustrated herein is just one of many different surgical devices and designs with which the present disclosures can be used. The description of the same is for illustrative purposes to provide one way by which the end effector assemblies can be attached to a device and actuated. The description of the device 100 in no way limits the ability for the end effector assemblies described herein to be used in conjunction with many other devices and systems. Accordingly, by way of non-limiting example, while in the illustrated embodiment the end effector assembly 130 is described as extending over the distal end 104d of the elongate shaft 104, in other instances, using any techniques known to those skilled in the art, the end effector assemblies of the present disclosures can be coupled directly to a distal tip of the elongate shaft 104, coupled in some fashion inside the distal end 104d of the elongate shaft 104, or coupled to a coupler, such as the coupler 270, 270', which itself is coupled in some fashion to the elongate shaft 104. Any way by which the jaws of the present disclosure can be actuated is acceptable. Other examples of surgical devices that a person having ordinary skill in the art could use in conjunction with the present disclosures includes but are not limited to the devices provided for in U.S. Patent Application Publication No. 2011/0087267, entitled "Method for Exchanging End Effectors In Vivo," which is hereby incorporated by reference in its entirety.

Figure 7B:
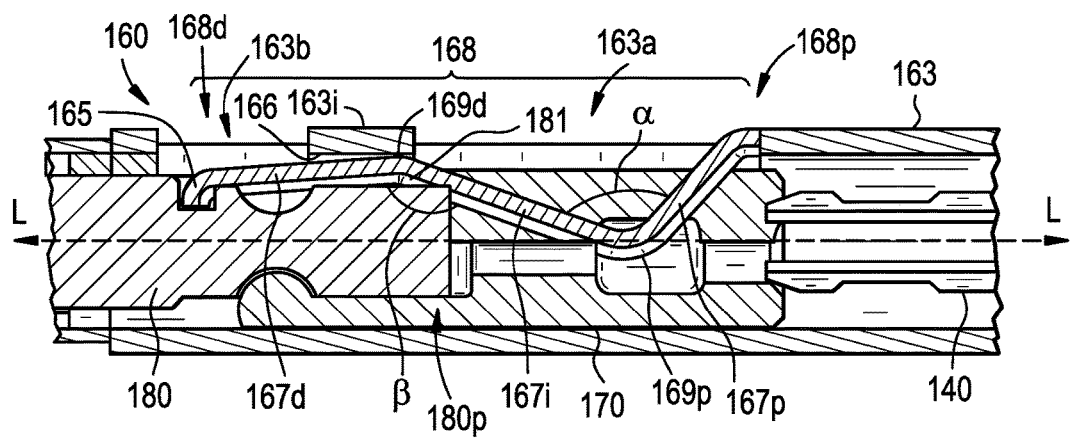
FIG. 7B is a side, detailed, cross-sectional view of the end effector assembly of FIG. 7A taken along a line B-B, the end effector assembly having a lock spring in a ready-to-attach position when an intermediate shaft of the surgical device is not fully coupled to the end effector assembly.

FIG. 7A shows the end effector assembly 160 of FIGS. 1A and 1B. The end effector assembly 160 can be configured in a similar manner as described above with respect to the end effector assembly 260 of FIG. 5, and thus can include, by way of non-limiting examples, an attachment arm or receiving sleeve 162, an end effector receiver or coupler 170 (FIGS. 7B and 7C) at least partially disposed within the attachment arm 162, and an end effector 180. In the illustrated embodiment, a distal portion 162d of the attachment arm 162 includes a lock spring 168, which is a feature that assists in maintaining a location of an end effector (e.g., end effector 180) with respect to the attachment arm 162 when a surgical device is not coupled with the end effector assembly 160. The lock spring 168 also provides a notification feature to inform a user both when the end effector assembly 160 is ready to be attached to the outer shaft 104 because the end effector 180 is properly secured to the end effector assembly 160, and when the end effector assembly 160 is properly secured to a surgical device for subsequent operation of the end effector 180 by the surgical device. As shown, the lock spring 168 is disposed in the distal portion 162d of the attachment arm 162, and is configured to be moved between an initial, ready-to-load configuration, illustrated in FIG. 7B, and a coupled, ready-to-actuate configuration, illustrated in FIG. 7C.

The lock spring 168 has a proximal arm 167p connected to an intermediate arm 167i by a proximal hinge 169p, with the intermediate arm 167i being connected to a distal arm 167d by a distal hinge 169d. Each hinge 167p, 169d is flexible such the arms 167p, 167i, 167d can be deflected with respect to each other at the hinges 169p, 169d. In the illustrated embodiment, the intermediate arm 167i is longer than the distal arm 167d and the distal arm 167d is longer than the proximal arm 167p, but other configurations are possible. Further, in the illustrated embodiment an angle α between the proximal and intermediate arms 167p and 167i at the proximal hinge 169p in the initial configuration shown in FIG. 7B can be in the range of about 90 degrees to about 130 degrees, and in one embodiment it can be about 100 degrees, while the angle α in the coupled, ready-to-actuate configuration shown in FIG. 7C can be in the range of about 130 degrees to about 170 degrees, and in one embodiment it can be about 160 degrees. Still further, in the illustrated embodiment, an angle β between the intermediate and distal arms 167i and 167d at the distal hinge 169d in the initial configuration shown in FIG. 7B can be in the range of about 140 degrees to about 175 degrees, and in one embodiment it can be about 170 degrees, while the angle β in the coupled, ready-to-actuate configuration shown in FIG. 7C can be in the range of about 181 degrees to about 210 degrees, and in one embodiment it can be about 195 degrees.

A proximal end 168p of the lock spring 168 can be coupled to a portion of the end effector assembly 160, such as a portion of an outer wall 163, and the proximal and distal hinges 169p, 169d can be positioned so that they can be contacted and deflected. As shown, in the initial configuration provided for in FIG. 7B, the proximal hinge 169p can be disposed within an axial path of the intermediate shaft 140 so that it can be engaged and deflected by distal advancement of the intermediate shaft 140, and the distal hinge 169d can be disposed adjacent to a portion of an inner sidewall 166 of the end effector assembly 160 so that it can be engaged and deflected by the inner sidewall 166 of the end effector assembly 160. A distal end 168d of the lock spring 168 can include an engagement feature, as shown a latch 165, that can be configured to engage a complementary portion of the proximal portion 180p of the end effector 180 when the end effector 180 is attached to the coupler 170 but the end effector assembly 160 is not coupled to a surgical device, i.e., the initial configuration as shown in FIG. 7B. The latch 165 can be disengaged from the end effector 180 in the coupled, ready-to-actuate configuration, as shown in FIG. 7C.

The end effector assembly 160 can include one or more openings 163a, 163b formed in its outer wall 163 so that portions of the lock spring 168 can be visible to the user. As shown, a first, more proximal opening 163a is formed such that the proximal and intermediate arms 167p, 167i of the lock spring 168 are visible, and a second, more distal opening 163b is formed such that the distal arm 167d of the lock spring 168 is visible. A portion of the inner sidewall 166 that is opposed to a part of an intermediate portion 163i of the outer wall 163 disposed between the two openings 163a, 163b serves as the deflecting surface for the distal hinge 169d.

Figure 7C:
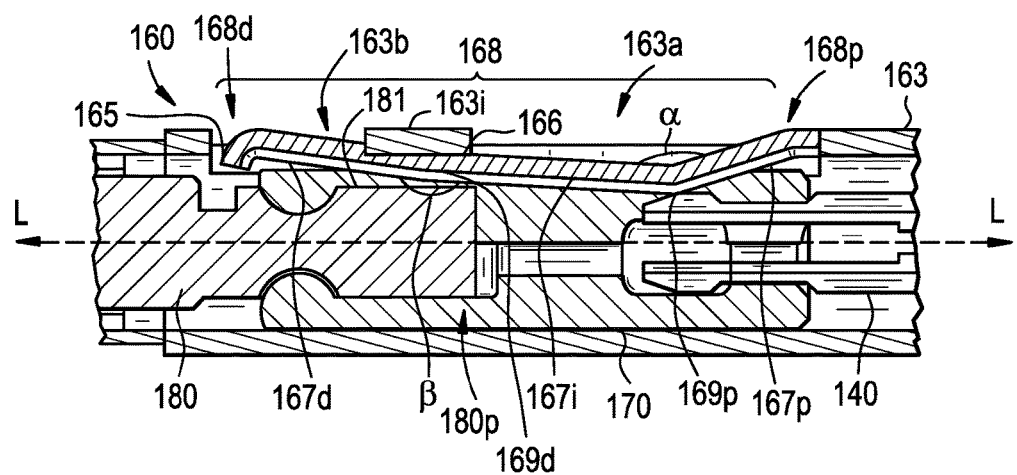
FIG. 7C is the side, detailed, cross-sectional view of the end effector assembly of FIG. 7B with the lock spring in a disengaged position by virtue of the intermediate shaft being fully coupled to the end effector assembly.

The location of portions of the lock spring 168 can help notify a user when the end effector assembly 160 is in the initial, ready-to-load configuration illustrated in FIG. 7B and the coupled, ready-to-actuate configuration in FIG. 7C. Further, portions of the lock spring 168 that are visible through the openings 163a, 163b can be colored to assist in such notification. More specifically, when the lock spring 168 is in the ready-to-actuate configuration, portions of the proximal, intermediate, and distal arms 167p, 167i, 167d are all advanced away from the longitudinal axis L and towards the openings 163a, 163b, making them more visible. This greater visibility can be accentuated by making the visible outer surfaces of the lock spring 168 a different color than the end effector assembly outer wall 163. In the illustrated embodiment, a top portion of the latch 165 extends radially beyond the outer wall 163 to make it easy for the user to see that the end effector assembly 160 is properly secured to the surgical device 100 and thus the ready-to-actuate configuration has been achieved. As a result, the possibility of inadvertently thinking the end effector 180 is properly coupled to the device 100 when it is not is greatly diminished. The lock spring 168 can also provide an audible indication to the user when it is deflected to further identify for the user the configuration of the end effector 180 with respect to the end effector assembly 160 and the end effector assembly 160 with respect to the surgical device 100. When a user hears the audible deflection of the hinges 169p, 169d, the user can be assured that a particular configuration has been achieved.

In use, as the intermediate shaft 140 is advanced distally into the end effector assembly 160 and enters the coupler 170, it can engage a surface of the proximal arm 167p and then the proximal hinge 169p. As the intermediate shaft 140 continues to advance distally, the proximal hinge 169p is deflected radially outward by the shaft 140, i.e., away from the longitudinal axis L of the end effector assembly 160 (which is co-linear with the longitudinal axis L of the intermediate shaft 140 in the illustrated embodiment), causing the portions of the proximal and intermediate arms 167p, 167i directly adjacent to the proximal hinge 169p to also deflect radially outward, i.e., towards the proximal opening 163a. This movement also causes the distal hinge 169d to advance radially outwards, pressing into the inner sidewall 166 of the intermediate portion 163i of the outer wall 163. The force supplied by the inner sidewall 166 then forces the distal hinge 169d to deflect radially inwards, i.e., towards the longitudinal axis L, causing the portions of the intermediate and distal arms 167i, 167d directly adjacent to the distal hinge 169d to also deflect radially inward. This movement, however, is restricted by an outer surface 181 of the proximal end 180p of the end effector 180, which in turn results in a distal end 167d of the distal arm 167d, including the latch 165, to deflect radially outward, i.e., towards the distal opening 163b. When the latch 165 advances radially outward, it disengages the end effector 180, but the end effector 180 is held by the intermediate shaft 140 and the inner shaft 130 (not shown) because the device 100 and the end effector assembly 160 are now in the ready-to-actuate configuration. As such, the surgical device 100 can be operated to control the end effector 180 as described herein or otherwise known to those skilled in the art.

The end effector assembly 160 can likewise be de-coupled from the surgical device 100 by proximally retracting the intermediate shaft 140 and the inner shaft 130 (not shown). This can cause the hinges 169p, 169d to return to their positions in the initial configuration, thus returning the arms 167p, 167i, 167d of the lock spring 168 to their positions in the initial configuration, including having the latch 165 hold the end effector 180. A user can manually push the lock spring 168 to disconnect the end effector 180 from the end effector assembly 160 as desired, or other techniques for disassociating the end effector 180 from the end effector assembly 160 that are described herein or otherwise known to those skilled in the art can be used. A person skilled in the art will also recognize a number of other configurations that the lock spring 168 can have to provide notification to certain configurations and to hold the end effector 180 with respect to the end effector assembly 160 without departing from the spirit of the present disclosure. For example, the lock spring 168 can have more or less hinges and arms, and/or the hinges and arms can be configured to be sized, angled, and deflectable in other manners.

End effector assemblies like the end effector assemblies 160 and 260 can be presented to surgical devices for coupling thereto using a variety of devices and techniques known to those skilled in the art. In some exemplary embodiments an end effector loading device or loader 1000 is provided to deliver end effector assemblies to the surgical device 100, as shown in FIG. 8.

The outer shaft 104 and associated components of the surgical device 100 are inserted through one lumen formed in the body to deliver the distal end 100d of the surgical device 100, including distal ends 104d, 140d of the outer and intermediate shafts 104, 140, to a surgical site. Meanwhile, the loading device 1000 is inserted through a second, separate lumen formed in the body to deliver a distal end 1000d of the loading device 1000 to the surgical site. The loading device 1000 includes a housing or handle 1002, a shaft 1004 extending distally therefrom and being cannulated therethrough, and an articulating distal portion 1020, also referred to herein as a delivery chamber or delivery end.

The articulating distal portion 1020 can be controlled by one or more actuators, such as actuator 1006 associated with the housing 1002 and configured to operate internal components disposed in the housing 1002 that move the articulating distal portion 1020 from a position substantially aligned with a longitudinal axis $L_2$ of the loader 1000, some referred to herein as a longitudinally-aligned configuration, to the articulated position illustrated in FIG. 8. The angle γ illustrates an amount of rotation by the articulating distal portion 1020 from its aligned, entry configuration to its articulated, delivery configuration. The amount of rotation can be between about 0 degrees to about 170 degrees, and in one embodiment the amount of rotation is between about 0 degrees to about 150 degrees, although other degrees of rotation can be possible, depending, at least in part, on the configuration of all of the components of the loading device 1000, the type of procedure being performed, the anatomy of a patient, and the preferences of the surgeon.

A pivot joint 1040 can couple the delivery chamber 1020 to the shaft 1004 and the delivery chamber 1020 can be angulated relative to the shaft 1004 by engaging actuator(s) on the housing 1002. As will be discussed in greater detail below, the delivery chamber 1020 can be configured to releasably hold an end effector assembly (not shown in FIG. 8) and to present the end effector assembly to a surgical instrument 100. In some of the illustrated embodiments described herein, when the end effector assembly is coupled to the loading device 1000, an attachment arm (not shown in FIG. 8) of an end effector assembly is positioned adjacent to a distal end 1020d of the delivery chamber 1020, with the end effector itself being disposed further proximally in the chamber 1020.

The loading device 1000 is shown in greater detail in FIGS. 9A-10B. The loading device 1000 can include the housing 1002 and the rigid and substantially straight outer shaft 1004. Alternatively, other configurations of housings and shafts are possible, including having a shaft that is curved and/or flexible, which would be beneficial for introducing the shaft into a natural orifice. The articulating delivery chamber 1020 can be controlled by one or more actuators, such as a slider 1006 disposed on the handle 1002 of the loader 1000. As will be appreciated, the delivery chamber 1020 can be articulated prior to or after it is inserted into a surgical site. The pivot joint 1040 can couple the articulating distal portion 1020 to the shaft 1004. The distal portion 1020 can be angulated relative to the shaft 1004 by engaging the slider 1006 and moving the slider 1006 relative to the housing 1002, for instance in a direction E.

As previously mentioned, the loader 1000 can be configured to hold an end effector assembly 360 (FIG. 9B) therein and to present the end effector assembly 360 for loading onto the shaft 104 of the instrument 100. As will be appreciated, most any end effector can be used in conjunction with the end effector assembly, and most any end effector assembly can be used in conjunction with the loader 1000. The delivery chamber 1020 can have many different configurations, which can depend, at least in part, on the size and shape of the other components with which it is used (e.g., the surgical device, the end effector assembly, and the other components of the loader), the patient (e.g., pediatric, adult, size, weight, etc.), and the type of procedure being performed. In the illustrated embodiment, the delivery chamber 1020 has a substantially cylindrical shape with an opening 1022 formed through a majority of its length. The opening starts at a distal end 1020d of the delivery chamber 1020 and can extend far enough into the chamber 1020 to allow an end effector assembly to be disposed therein. The opening 1022 allows for the end effector assembly to be removed from the loading device 1000 and attached to a surgical device for subsequent use.

While a terminal end surface or distal-most outer wall 1024 of the delivery chamber 1020 that defines the opening 1022 can have a variety of sizes and shapes, in the illustrated embodiment it has a three-dimensional shape in which one portion 1024a extends more distal from a proximal end 1020p of the chamber 1020 than another portion 1024b does. More particularly, as shown, the first portion 1024a extends further away from the proximal end 1020p along the longitudinal axis $L_2$ than the second portion 1024b extends away from the proximal end 1020p along the longitudinal axis $L_2$. This three-dimensional footprint or shape can assist a user in identifying a location of the distal end 1000d of the loading device 1000 in vivo because a user can more easily determine a location of a shaft of the surgical device (e.g., the shaft 104 of the surgical device 100) with respect to the loading device 1000. When a terminal end surface of a loading device is two-dimensions, such as being circular and having no portion that extends more distal than another, and a user contacts that surface with a shaft of a surgical device, it is more difficult for a user to know if the shaft needs to be moved up, down, left, or right to pass into the delivery chamber of the loading device as compared to the disclosed three-dimensional configuration of the terminal end surface. This is at least because the three-dimensional shape provides additional feedback for the user to assist by informing the user how the shaft of the surgical device should be manipulated to pass into the delivery chamber.

Any number of three-dimensional shapes can be used in view of the present disclosures, but in the illustrated embodiment the terminal end surface 1024 has a troughed, scallop shape in which a width of the first and second portions 1024a, 1024b is greater than a width of an intermediate portion 1024i of the terminal end surface 1024. In some exemplary embodiments, the first portion 1024a is approximately in the range of about 2 to about 20 millimeters longer than the second portion 1024b at their distal most ends, and in one exemplary embodiment that difference in length is about 5 millimeters. Further, in some exemplary embodiments, a width $w_1$ (labeled in FIG. 10A) of the first and second portions 1024a, 1024b is approximately in the range of about 2 to about 10 millimeters, while a width $w_2$ (labeled in FIG. 10A) of the intermediate portion 1024i is approximately in the range of about 1 to about 8 millimeters, and in one exemplary embodiment the widths $w_1$ of the first and second portions 1024a, 1024b is about 5 millimeters and the width $w_2$ of the intermediate portion 1024i is about 3 millimeters. In other embodiments, the widths of the first and second portions 1024a, 1024b can be different from each other.

Further, the delivery chamber 1020 can include one or more engagement features for holding an end effector assembly therein, as described in this paragraph and in alternative embodiments further below. By way of non-limiting example, in some exemplary embodiments, the engagement feature includes a plurality of leaf springs (not shown) disposed within the delivery chamber 1020. The leaf springs can provide an interference fit with an end effector assembly to frictionally hold the end effector assembly in the delivery chamber 1020. In the illustrated embodiment, as shown in FIG. 9B, when an end effector assembly 360 is loaded in the delivery chamber 1020, a distal end (not shown) of the end effector assembly, i.e., the distal tip of the end effector, is positioned closest to the pivot joint 1040, and a proximal end 360p, i.e., a terminal end of an attachment arm or receiving sleeve 362, is positioned closest to the terminal end surface 1024. This arrangement prevents jaws (not shown) of an end effector (not shown) of the end effector assembly 360 from opening when the end effector assembly 360 is positioned within the delivery chamber 1020.

The housing 1002 of the loading device 1000 can have various configurations. For example, the housing 1002 can include one or more recesses and/or can be contoured along a proximal, lower surface 1008 thereof to facilitate being grasped by a user's hand. The actuator/slider 1006 can also be contoured along an outer surface thereof or can include a recess or depression 1007 having one or more surface features that facilitate friction between a user's fingers and/or thumb and the slider. An elongate track 1010 can be formed on a central, upper surface 1009 of the housing 1002 and the slider 1006 can move proximally and distally along the track 1010.

Figure 9C:
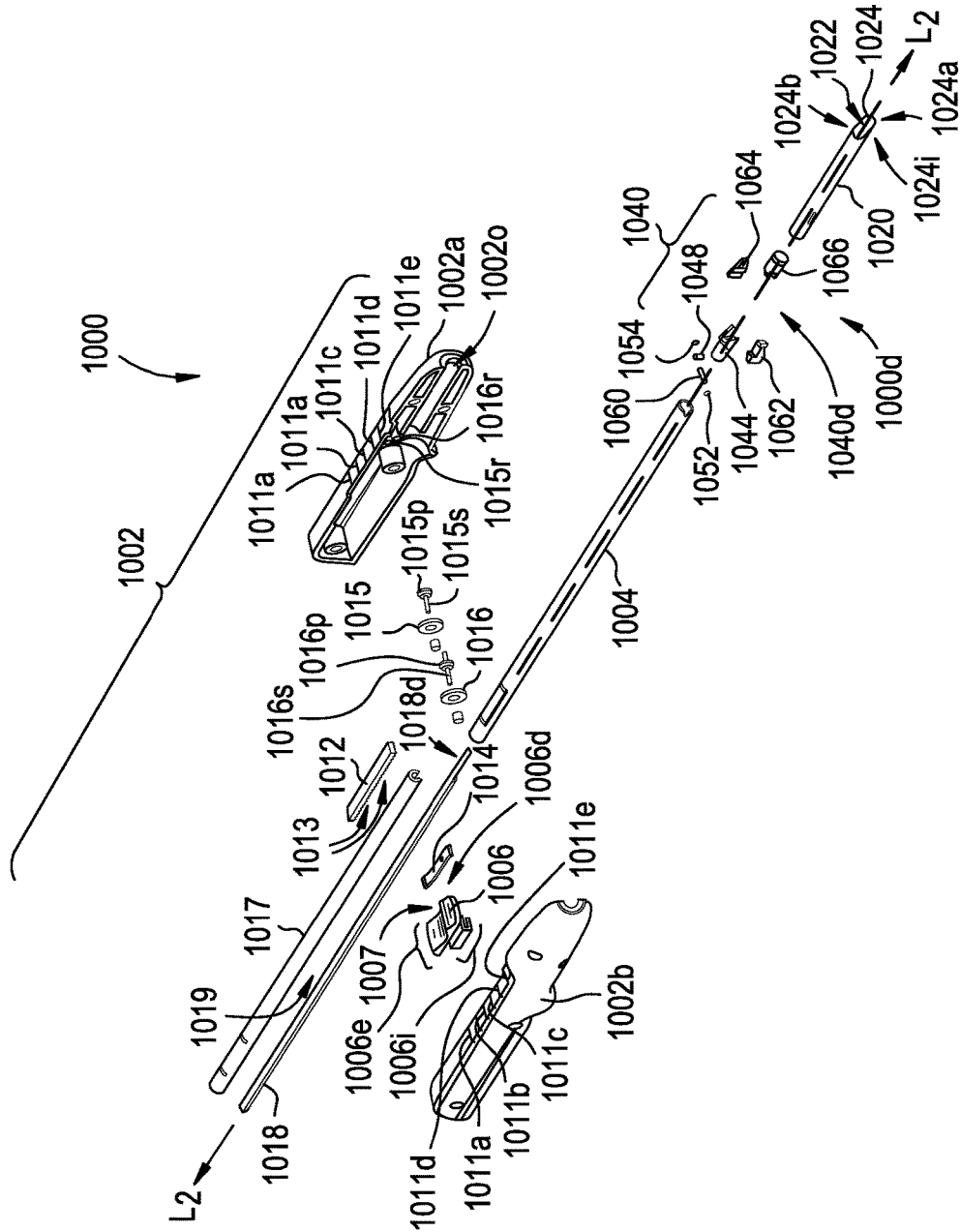
FIG. 9C is a perspective, exploded view of the loading device of FIG. 9A.

As shown in FIG. 9C, the track 1010 can include a plurality of markings spaced at equal distances apart along the track, such as five markings 1011a, 1011b, 1011c, 1011d, 1011e. Though not shown, each of the markings can be labeled to assist a user with monitoring a degree of articulation of the articulating delivery chamber 1020 relative to the elongate shaft 1004. For example, proximal marking 1011a can be labeled 0 degrees and second marking 1011b that is adjacent and distal to the proximal marking 1011a can be labeled 30 degrees. For another example, in loading devices where the articulating delivery chamber is configured to be angled in two different directions relative to the elongate shaft, a central marking (such as the marking 1011c) can be labeled 0 degrees to indicate that the delivery chamber is axially aligned with the elongate shaft. In some embodiments, the proximal markings can be labeled with positive angles and the distal markings can be labeled with negative angles to reflect both the degree of articulation of the distal portion as well as the direction of articulation. As will be appreciated, the number of markings, the particular spacing between the markings, and the degree of articulation of the delivery chamber 1020 relative to the shaft 1004 can vary but can be generally selected so that the when a distal end 1006d of the slider 1006 is positioned adjacent to one marking, the marking corresponds to and accurately informs a user as to the degree of articulation of the delivery chamber 1020.

FIG. 9C illustrates the housing 1002 of the loading device 1000 in greater detail. The device 1000 includes the actuator slider 1006 having an external portion 1006e that can be positioned outside of and external to the housing 1002 and directly contacted by a user, and an internal portion 1006*i* that can mate with various internal actuation components. For example, the internal portion 1006*i* can have a first lateral recess that can receive an actuator rack 1012 therebetween and a second lateral recess that can engage a slider detent spring 1014 that can engage with one or more recesses (e.g., detents disposed on an internal surface under each of the markings 1011*a*, 1011*b*, 1011*c*, 1011*d*, 1011*e*) to frictionally hold the slider 1006 in its current position even as the delivery chamber 1020 is being articulated. These recesses or detents can also provide tactile and/or audible feedback to a user to indicate that the slider 1006 is locked relative to the track 1010. The locking of the slider 1006 relative to the track 1010 permits incremental articulation of the delivery chamber 1020 relative to the elongate shaft 1004, and can also prevent back drive of the delivery chamber 1020 that might otherwise occur when forces are applied to the delivery chamber 1020 during a surgical procedure. The actuator rack 1012 can be disposed in the housing 1002 and can have a rectangular cross-sectional shape with teeth 1013 formed on at least one of its outer surfaces. When the actuator rack 1012 is received in the first lateral recess of the slider 1006, the teeth 1013 can be oriented toward the lower surface of the housing 1002. The slider 1006 and the actuator rack 1012 can move together as a unit such that moving the slider 1006 proximally/distally along the track 1010 causes the actuator rack 1012 to move in the same direction.

The actuator rack 1012 can interact with other actuation components to facilitate articulation of the distal chamber 1020. As shown, a first drive gear 1015 can be disposed in the housing 1002, can mesh with the actuator rack 1012, and can rotate about a first gear shaft 1015*s*. The first gear shaft 1015*s* can be received in and can rotate relative to a first shaft recess 1015*r* formed in the housing 1002. The first drive gear 1015 can be laterally offset from the central longitudinal axis $L_2$ extending through the housing 1002 and through the elongate shaft 1004. A first pinion 1015*p* can rotate along with the first drive gear 1015 on the first gear shaft 1015*s* and can also be laterally offset from the central longitudinal axis $L_2$. The first pinion 1015*p* can mesh with a second drive gear 1016 disposed on a second gear shaft 1016*s*, the second gear shaft 1016*s* being received in and configured to rotate relative to a second shaft recess 1016*r* formed in the housing 1002. A second pinion 1016*p* can be disposed on the second gear shaft 1016*s* and the second pinion 1016*p* can rotate with the second drive gear 1016. The second pinion 1016*p* can be axially aligned with the central longitudinal axis $L_2$ and can mesh with teeth 1019 formed on a driving rack 1018 such that rotational motion of the pinion 1016*p* causes the rack 1018 to advance linearly in a proximal or distal direction. The first and second drive gears 1015, 1016 can have the same diameter and number of teeth or in other aspects can have different diameters and/or number of teeth such that the rotation is mechanically advantaged. As will be appreciated, the particular gear mechanisms in the housing can vary.

The housing 1002 can include first and second portions 1002*a*, 1002*b* that can be selectively detached from one another to reveal the internal actuation components. Such a configuration is also conducive to fixing, cleaning, or replacing components disposed in the housing 1002, or for doing the same to the housing 1002 itself. As shown, the outer elongate shaft 1004 of the loading device 1000 can be received in an elongate opening 1002*o* formed in the housing 1002 and can extend along the central longitudinal axis $L_2$. A rack guide 1017 can be disposed within the elongate shaft 1004 and can extend distally from the housing/handle portion 1002. The rack guide 1017 can have a substantially elongate cylindrical shape that allows the rack guide 1017 to be disposed within and remain fixed relative to the elongate shaft 1004. The rack guide 1017 can have a recess formed thereon, such as a rectangular shaped cutout formed along a longitudinal length thereof, sized and shaped to receive the driving rack 1018. The driving rack 1018 can have teeth 1019 formed on a first lateral surface. The driving rack 1018 can be longer than the elongate shaft 1004 such that the driving rack 1018 can extend between and move relative to the elongate shaft 1004 and the housing 1002 to articulate the articulating distal portion 1020.

Figure 10A:
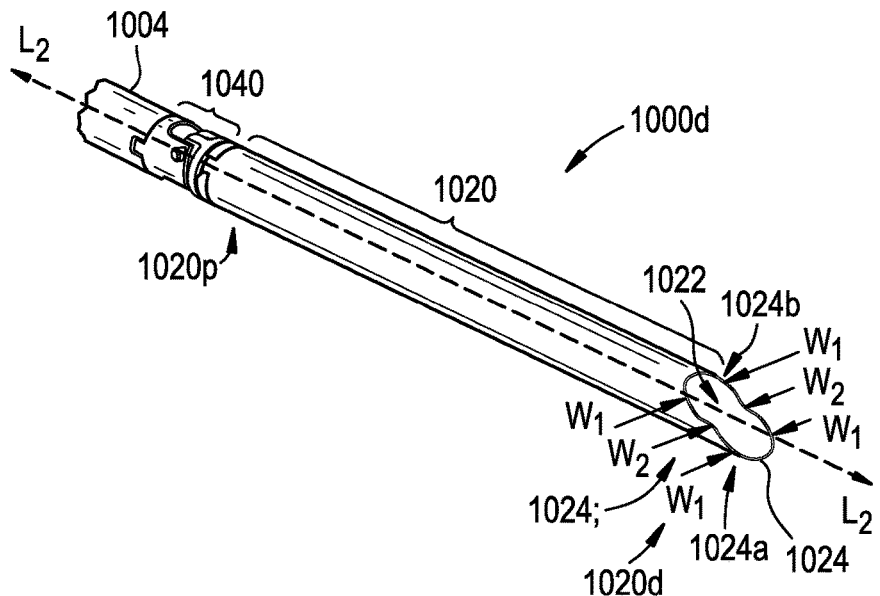
FIG. 10A is a perspective, detailed view of a distal end of the loading device of FIG. 9A, the loading device having a delivery chamber disposed in a longitudinally aligned configuration.
Figure 10B:
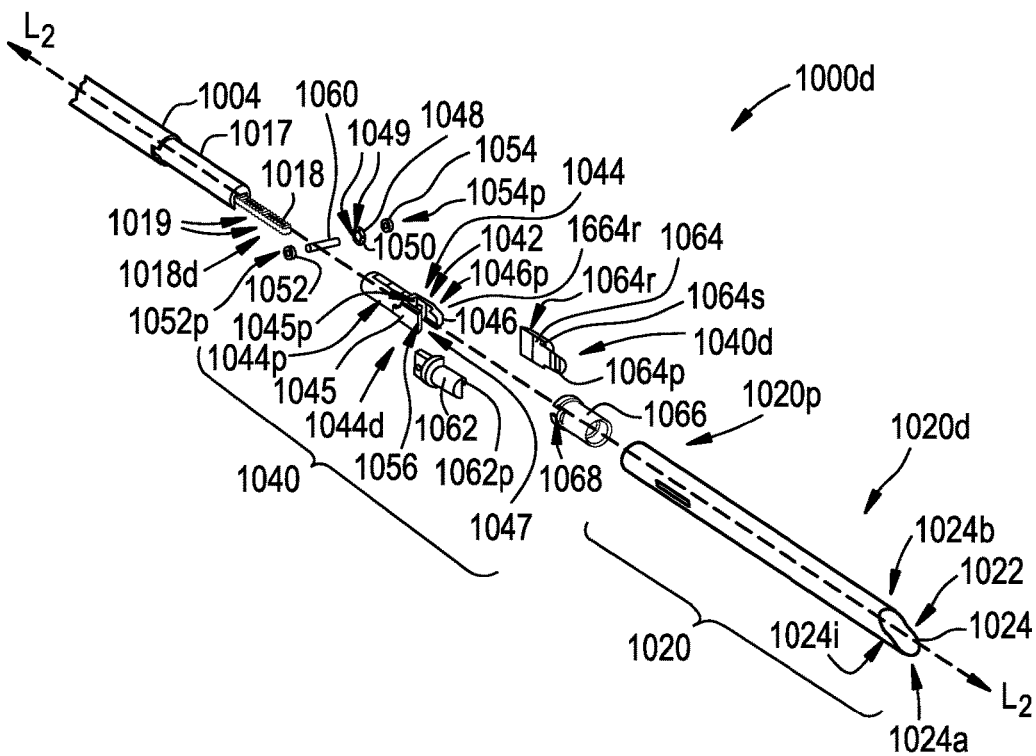
FIG. 10B is a perspective, exploded view of the distal end of the loading device of FIG. 10A.

FIGS. 9C and 10B illustrate components of the pivot joint or hinge 1040 and their interaction with the driving rack 1018 that extends from the housing 1002. A distal portion 1018*d* of the driving rack 1018 can have the teeth 1019 disposed on a surface that faces toward the slider 1006 and faces toward an upper surface of the housing 1002. As will be appreciated, the driving rack 1018 can couple from the housing 1002 to the pivot joint 1040 or one or more intermediate rods or racks can extend through the elongate shaft 1004 and operably couple the driving rack 1018 to the internal actuation components of the housing 1002. The distal portion 1018*d* of the rack 1018 can be received in an elongate opening 1042 formed in a coupler 1044 that forms a proximal portion 1040*p* of the pivot joint 1040. The coupler 1044 can have a proximal end 1044*p* and a distal end 1044*d*, the proximal end 1044*p* mating with the distal end 1004*d* of the elongate outer shaft 1004. The distal end 1044*d* can have first and second arm portions 1045, 1046 defining a substantially U-shaped space 1047 therebetween for receiving articulation mechanisms that allow the delivery chamber 1020 to pivot about the pivot joint 1040 and hold the delivery chamber 1020 in an articulated position. For example, the articulation mechanisms can include a modified spur gear 1048 (which can also be referred to as a modified pinion) having teeth 1049 formed around a first portion of its outer circumference and having a substantially planar surface 1050 formed around a remaining portion of the outer circumference of the gear 1048. The teeth 1049 of the spur gear 1048 can be spaced apart along about 50% to about 75% of the circumference of the gear 1048, although other configurations, including those in which the teeth are formed along the entire circumference of the gear 1048, are possible.

The pivot joint 1040 can include first and second deformable washers 1052, 1054, and the washers 1052, 1054 can act as secondary holding features to the spur gear 1048 to hold the delivery chamber 1020 in an articulated position. The washers 1052, 1054 can each have central openings extending therethrough. A plurality of protrusions 1052*p*, 1054*p* can be formed around and spaced along a first hemisphere of an outer face of each of the washers 1052, 1054, respectively, and a second hemisphere of the outer face of each of the washers 1052, 1054 can be substantially planar and smooth, lacking any protrusions. The protrusions 1052*p*, 1054*p* can be equal to or slightly larger in size than a plurality of recesses 1045*p*, 1046*p* (described below) formed on inner surfaces of the arm portions 1045, 1046 of the coupler 1044 so that the protrusions 1052*p*, 1054*p* of the respective washers 1052, 1054 frictionally engage with the respective recesses 1045*p*, 1046*p* and apply a biasing force that holds the washers 1052, 1054 in position relative to the arm portions 1045, 1046. The arrangement of the plurality of protrusions 1052*p*, 1054*p* on only one hemisphere of each of the washers 1052, 1054 in the illustrated embodiment can permit 90 degrees of articulation of the articulating distal portion 1020 relative to the elongate shaft 1004 of the loader 1000. Further details about the deformable washers, and about a loading device and how the various components of a loading device work together to operate, pivot, etc., are provided in U.S. application Ser. No. 14/836,069, filed on Aug. 26, 2015, and entitled "Surgical Device having Actuator Biasing and Locking Features," which is hereby incorporated by reference in its entirety.

Referring back to the coupler 1044, an opening 1056, 1058 can be formed in each of the first and second arm portions 1045, 1046 of the coupler 1044, respectively, and can extend through inner and outer surfaces of the arm portions 1045, 1046. The openings 1056, 1058 can be formed on a lower portion of the arm portions 1045, 1046 that is below the central longitudinal axis $L_2$ which also extends centrally through the coupler 1044 such that the openings 1056, 1058 are offset from the central longitudinal axis $L_2$. The openings 1056, 1058 can be substantially circular-shaped or can be shaped in other ways known to those skilled in the art. A plurality of recesses 1045p, 1046p can be formed on the inner surface of the first and second arm portions 1045, 1046 around an entire circumference of each of the openings 1056, 1058, or around a portion of the circumference of the openings 1056, 1058. As described herein, the protrusions 1052p, 1054p formed on the outer faces of the washers 1052, 1054 can engage with the recesses 1045p, 1046p formed on inner surfaces of the arm portions 1045, 1046 to selectively angle the articulating distal portion 1020 with respect to the central longitudinal axis $L_2$.

The washers 1052, 1054 and the spur gear 1048 can be positioned between the first and second arm portions 1045, 1046 of the coupler 1044. Their respective central openings can be axially aligned with the openings 1056, 1058 formed in the arm portions 1045, 1046 and the spur gear 1048 can be positioned between the first and second washers 1052, 1054. A rod or pin 1060 can be inserted through the opening 1056 in the first arm portion 1045, through the central openings of the first and second washers 1052, 1054 and the spur gear 1048, and through the opening 1058 in the second arm portion 1046. The rod 1060 can thus mate these articulation components to the coupler 1044 and serve as the pivot of the pivot joint 1040. The rod 1060 and the washers 1052, 1054 can be offset from and positioned below the central longitudinal axis $L_2$. In some embodiments, the rod 1060 can include a plurality of keys formed along an outer surface thereof that can mate with corresponding recesses formed on an inner wall of each of the washers 1052, 1054 proximate to the central openings of the washers 1052, 1054 so that rotating the rod 1060 causes corresponding rotation of each of the washers 1052, 1054.

A distal portion 1040d of the pivot joint 1040 can include first and second pivotable hinge portions that can pivot as the spur gear 1048 and the deformable washers 1052, 1054 are rotated. For example, a first hinge portion 1062 and a second hinge portion 1064 can be detachable and can have a substantially cylindrical shape when positioned in a side-by-side relationship. The first and second hinge portions 1062, 1064 can be received in the space between the first and second arm portions 1045, 1046 of the coupler 1044. The first and second hinge portions 1062, 1064 can each have lateral planar surfaces formed therein that are configured to receive the driving rack 1018. Each of the first and second hinge portions 1062, 1064 can have an opening (not shown) formed in a proximal portion thereof and extending through and being perpendicular to outer and inner surfaces of the respective hinge portion. The openings can be configured to engage one of the first and second washers 1052, 1054 in a fixed mating relationship with the respective hinge portion 1062, 1064 such that rotation of the washers 1052, 1054 causes corresponding pivoting of the hinge portions 1062, 1064 relative to the coupler 1044.

The first and second hinge portions 1062, 1064 can be configured to mate with various components to help actuate the articulating distal portion 1020. In the illustrated embodiment, a distal portion of each of the first and second hinge portions 1062, 1064 can each have a protrusion 1062p, 1064p configured to mate with a corresponding slot formed on the distal end of an end effector assembly (not shown) or additional component of the loading device 1000. In the illustrated embodiment, the protrusions 1062p, 1064p of the hinge portions 1062, 1064 mate with an additional component of the loading device 1000 that is a tube 1066 having two L-shaped slots 1068 (only one of which is visible in FIG. 10B) to form a bayonet connection. As will be appreciated, various other types of mating features can be used to couple the hinge portions 1062, 1064 to the tube 1066, such as snap connections, threaded connections, and the like, including configurations provided for below.

The distal portion 1018d of the driving rack 1018 can mesh with the teeth 1049 of the spur gear 1048. The planar surface 1050 of the spur gear 1048 can contact a stop 1064s formed in the second hinge portion 1064, the stop 1064s being defined along a distal surface of a recess 1064r of the second hinge portion 1064. The first hinge portion 1062 can include a corresponding stop 1062s (not shown). This arrangement can allow proximal/distal movement of the driving rack 1018 to rotate the spur gear 1048 via the teeth 1019 of the driving rack 1048 engaging and meshing with the teeth 1049 of the spur gear 1048. Rotation of the spur gear 1048 can cause corresponding rotation of the hinge portions 1062, 1064 because of the stops 1062s, 1064s in the hinge portions 1062, 1064 contacting the planar surface 1050 of the spur gear 1048. Proximal movement of the driving rack 1018 can rotate the spur gear 1048 in a counter clockwise direction and distal movement of the driving rack 1018 can rotate the spur gear 1048 in a clockwise direction relative to the longitudinal axis $L_2$. This can cause corresponding rotation of the first and second washers 1052, 1054. Because the first and second washers 1052, 1054 are fixed relative to the first and second hinge portions 1062, 1064, the rotation of the washers 1052, 1054 can cause the first and second hinge portions 1062, 1064 to pivot in the direction of rotation relative to the elongate shaft 1004. The tube 1066 can be coupled to and positioned distal to the second hinge portion 1064 via the slot 1068 that receives the protrusion 1064p of the second hinge portion 1064. The tube 1066 can also pivot along with the first and second hinge portions 1062, 1064 due to this fixed mating relationship.

Figure 11A:
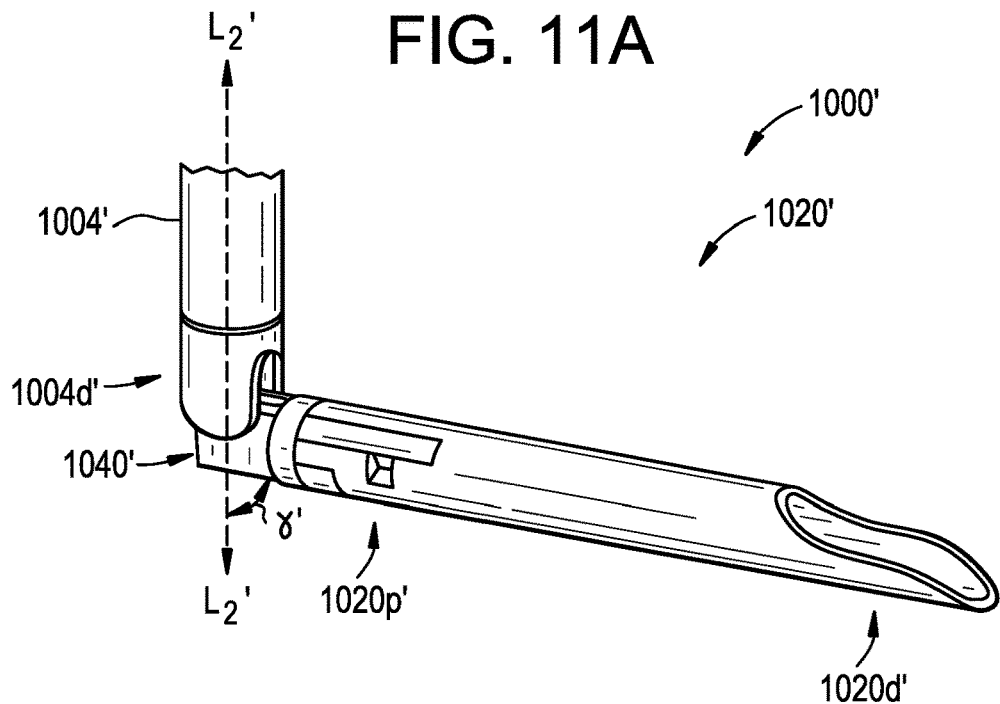
FIG. 11A is a perspective, detailed view of one exemplary embodiment of a distal end of a loading device, with a delivery chamber of the loading device being disposed in an articulated, loading configuration.
Figure 11B:
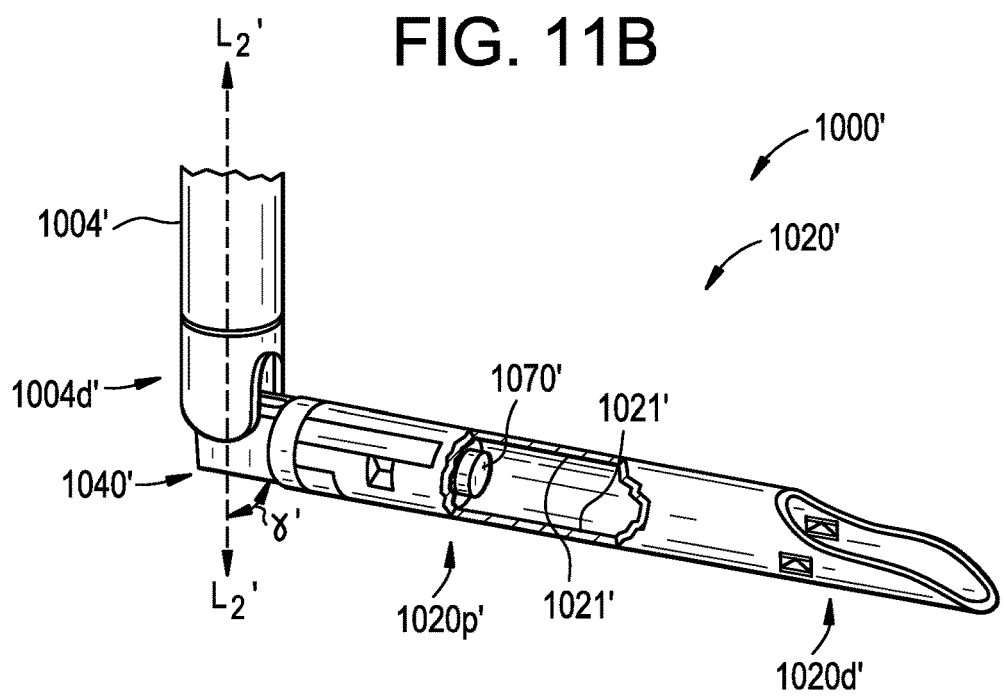
FIG. 11B is a perspective, detailed, partially transparent view of the distal end of the loading device of FIG. 11A.

An end effector assembly can be held within the delivery chamber 1020 using a variety of configurations and techniques, including the leaf springs described above, other configurations and techniques provided for herein, and other configurations and techniques known to those skilled in the art. FIGS. 11A and 11B provide one exemplary embodiment of using at least one magnet to maintain a location of an end effector assembly (not shown) with respect to a delivery chamber 1020'. The illustrated portion of a delivery device 1000' includes a distal end 1004d' of a shaft 1004', a pivot joint 1040', and the delivery chamber 1020' positioned in an articulated, loading configuration. As shown, a rare-Earth magnet 1070' having a generally circular profile is disposed in a proximal portion 1020p' of the delivery chamber 1020' and is configured to magnetically couple with an end effector of an end effector assembly to maintain a location of the end effector assembly within the delivery chamber 1020'. The magnet 1070' can also assist in seating the end effector assembly with a surgical device so the device can remove the end effector assembly from the delivery chamber 1020' and use it in conjunction with a surgical procedure. For example, as a shaft of a surgical instrument approaches an end of an attachment arm of an end effector assembly that is opposite to the location of the end effector itself, i.e., a proximal end of the attachment arm that is proximate to a distal end 1020d' of the delivery chamber 1020', the magnet 1070' can add its attraction force to the insertion force applied by the surgeon. The added attraction force from the magnet 1070' can help assure full seating between the end effector assembly and the surgical device occurs prior to removing the end effector assembly from the delivery chamber 1020'. Further, one or more magnets can also be provided in an inner sidewall 1021' of the housing of the delivery chamber 1020'. The magnet(s) can help to align or center an end effector assembly disposed therein with respect to the delivery chamber 1020' and/or to hold an end effector assembly within the delivery chamber 1020'.

Figure 12:
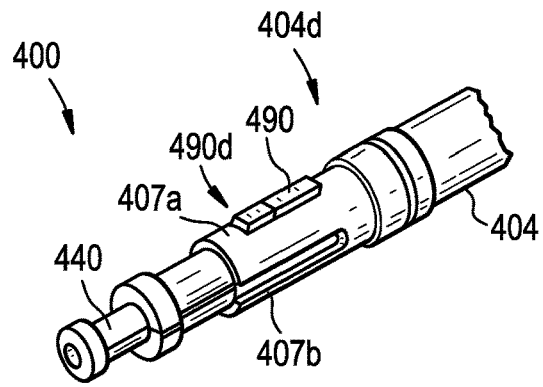
FIG. 12 is a perspective view of one exemplary embodiment of a distal end of a surgical device, the surgical device including intermediate and outer shafts.

In some embodiments, one or more magnets can be associated with a shaft of a surgical device to which the end effector assembly is to be coupled. The magnet(s) can provide an additional attractive force to disengage the end effector assembly from the delivery chamber and onto the shaft of the surgical device and/or it can help to align the end effector assembly with respect to the shaft so that they can be properly coupled together. Portions of a loading device and/or an end effector assembly can likewise be configured to be complementary to the magnet and geometries of the shaft of the surgical device. FIG. 12 provides one, non-limiting exemplary embodiment of a surgical device 400 having a magnet 490 associated with a distal end of a shaft 404, and FIGS. 13A-13C provide one, non-limiting exemplary embodiment of the surgical device 400 of FIG. 12 being used with a loading device 1400 and end effector assembly 460 that has features that are complementary to the surgical device 400.

As shown in FIG. 12, a magnetic key feature 490 is provided for on a distal portion 404d of an outer shaft 404. In the illustrated embodiment, the outer shaft 404 includes opposed deflectable arms 407a, 407b and the magnetic key feature 490 is coupled to or otherwise associated with one of the two arms 407a, 407b, as shown the arm 407a. The magnetic key feature 490 protrudes from an outer circumference of the outer shaft 404, has a rectangular cuboid shape, and has a positive pole on its distal end 490d. A person skilled in the art will recognize other configurations for the outer shaft 404 and the magnetic key feature 490 can be provided without departing from the spirit of the present disclosure, including but not limited to having more than one magnetic key feature, having the magnetic key feature(s) associated with a different part of the device (e.g., the intermediate shaft), the magnetic key feature(s) having a different shape, and/or the magnetic key feature(s) being a positive pole.

Figure 13A:
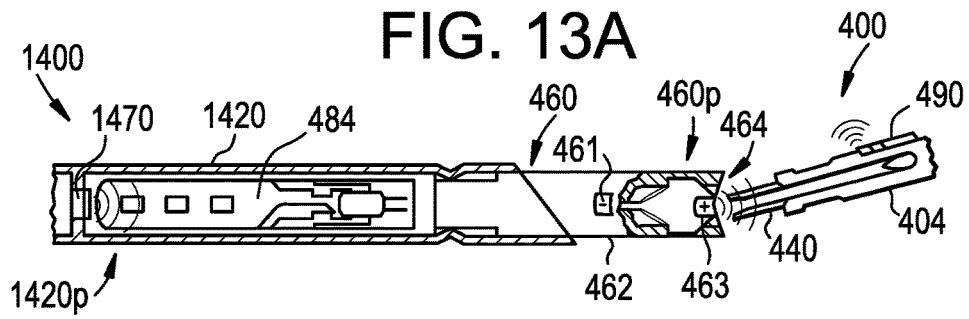
FIG. 13A is a side, partial cross-sectional view of the surgical device of FIG. 12 about to be inserted into one exemplary embodiment of a loading device having an end effector assembly disposed therein.
Figure 13B:
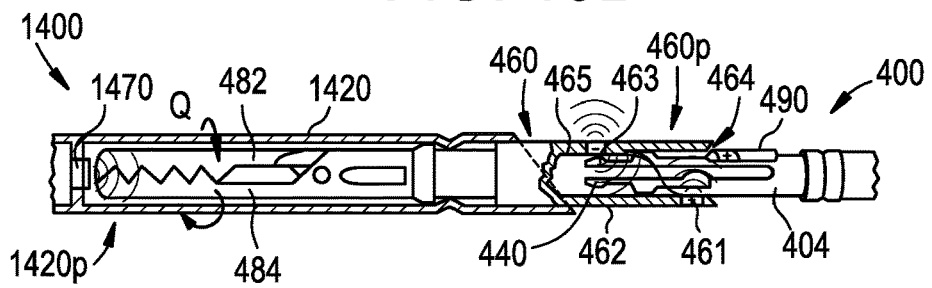
FIG. 13B is the side, partial cross-sectional view of the surgical device, loading device, and end effector assembly of FIG. 13A, with the surgical device being partially disposed within the end effector assembly.
Figure 13C:
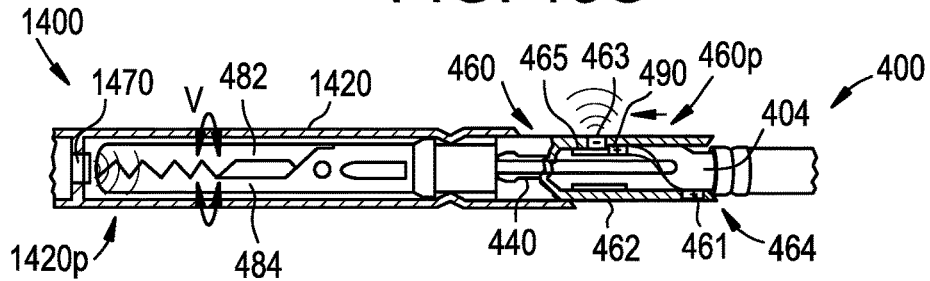
FIG. 13C is the side, partial cross-sectional view of the surgical device, loading device, and end effector assembly of FIG. 13B, with the surgical device being more fully disposed within the end effector assembly.

FIGS. 13A-13C illustrate a loading device 1400 having a delivery chamber 1420 with an end effector assembly 460 disposed therein, the delivery chamber 1420 and the end effector assembly 460 having configurations and features that are complementary in nature to the configurations and features of the surgical device 400, including its magnetic key feature 490. The end effector assembly 460 is maintained in the delivery chamber 1420 by a magnet 1470 disposed in a proximal portion 1420p of the chamber 1420 attracting magnetic properties of jaws 482, 484 of the end effector assembly 460. At a proximal portion 460p of the end effector assembly 460, a magnet 461 having a positive polarity is disposed near a terminal end of an attachment arm or receiving sleeve 462 of the end effector assembly 460, and a magnet 463 having a negative polarity is disposed further from the terminal end of the attachment arm 462, i.e., closer to the magnet 1470. As shown in FIG. 13B, as an intermediate shaft 440 and outer shaft 404 of the surgical device 400 are inserted through an opening 464 formed in the attachment arm 462, the positive polarity of the magnet 461 repels the positive polarity of the magnetic key feature 490. This causes the end effector assembly 460 to partially rotate and be aligned with respect to the surgical device 400 for subsequent attachment, as illustrated by the arrows Q, unless the end effector assembly 460 was already aligned. Although not illustrated, an inner shaft can also be used in conjunction with the intermediate and outer shafts 440, 404, similar to other configurations provided for herein that include each of an inner, intermediate, and outer shaft.

As the shafts 440, 404 are inserted further into the end effector assembly 460, the magnet 463 having the negative polarity attracts the magnetic key feature 490 due to the magnetic key feature's positive polarity. Further, geometries and configurations of the end effector assembly 460 and the shafts 440, 404 can assist in seating the end effector assembly 460 onto the outer shaft 404. As shown, a radially inward extending wall 465 can engage the magnetic key feature 490 to prevent further advancement of the shafts 440, 404 into the end effector assembly 460. Additional walls and grooves can be formed on the shafts 440, 404 and/or the inner wall 465 of the end effector assembly 460, among other places, to ease alignment thereof. As illustrated by the arrows V in FIG. 13C, the end effector assembly 460 can rotate slightly to allow the magnetic key feature 490 associated with the surgical device 400 to lock into position with respect to the end effector assembly 460.

Figure 14:
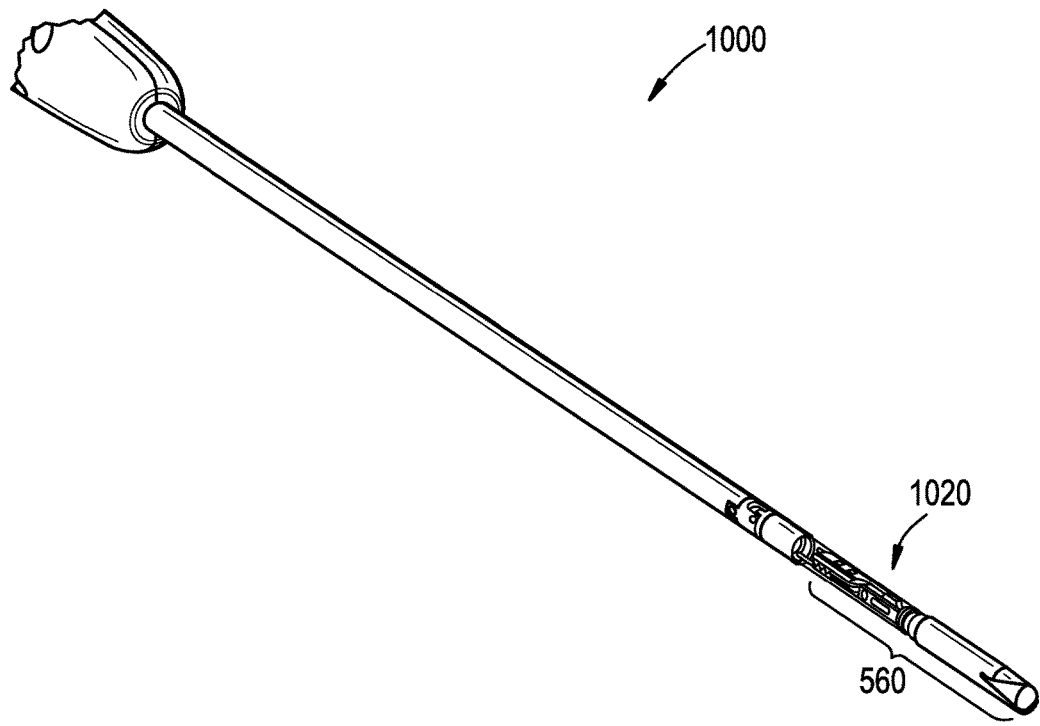
FIG. 14 is a perspective, partially transparent view of the loading device of FIG. 9A with a distal end of the loading device being transparent to illustrate one exemplary embodiment of an end effector assembly disposed therein.
Figure 15:
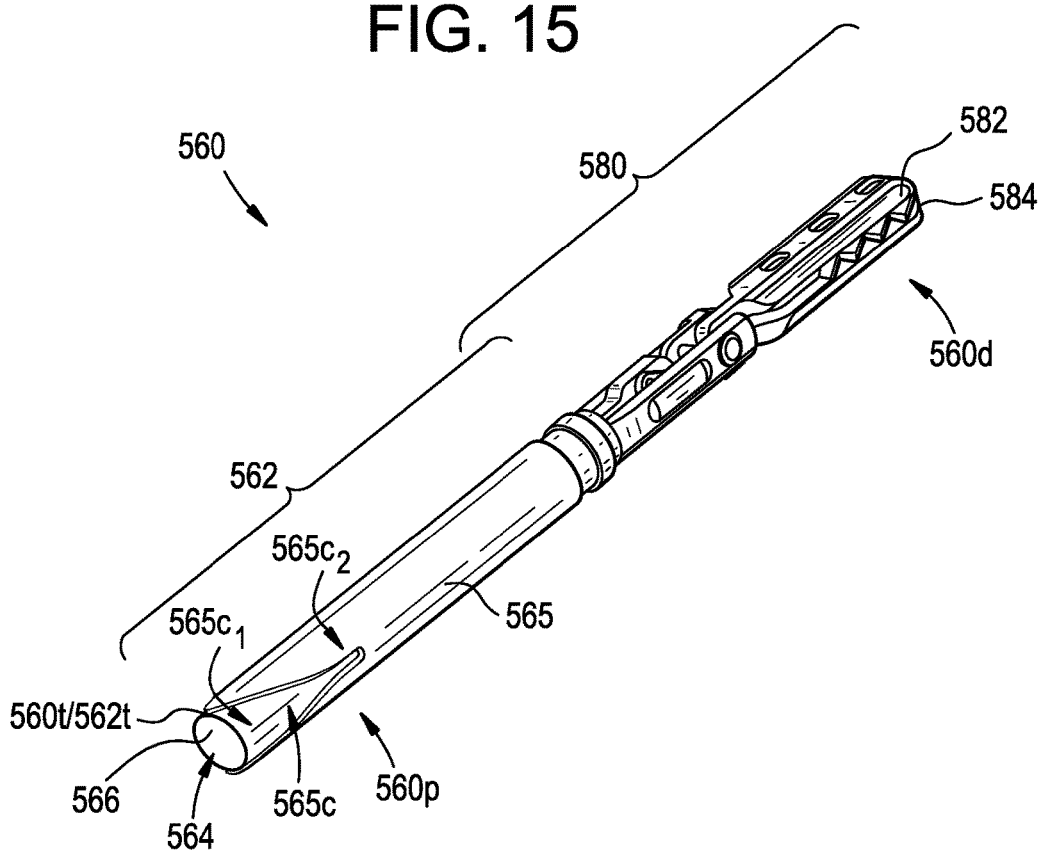
FIG. 15 is a perspective view of the end effector assembly of FIG. 14.
Figure 16:
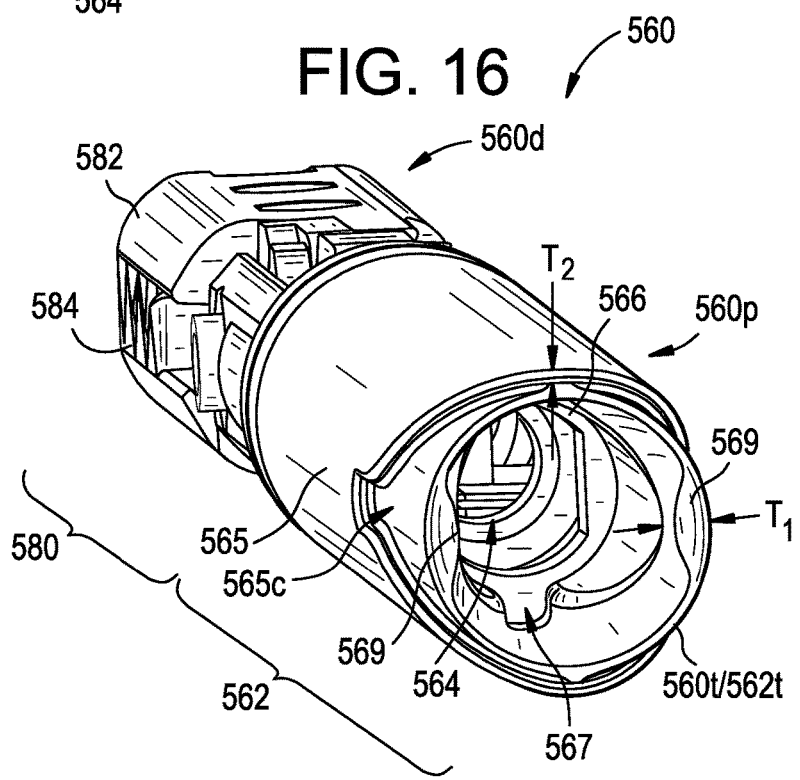
FIG. 16 is another perspective view of the end effector assembly of FIG. 15.

FIG. 14 illustrates an alternative configuration of an end effector assembly 560 that can be used in conjunction with the loading device 1000, or with other loading devices provided for or derivable from the disclosures herein, or otherwise known to those skilled in the art. The end effector assembly 560 can be configured to be disposed in the articulating distal chamber 1020, and it can be selectively coupled and de-coupled from a surgical device, like the surgical devices 100, 100', 400 provided for herein, derivable from the present disclosures, or otherwise known to those skilled in the art. FIGS. 15 and 16 illustrate the end effector assembly 560 in greater detail, FIGS. 17A and 17B illustrate another end effector assembly 560' in greater detail, and FIGS. 18A and 18B illustrate other ways of using some of the features of the end effector assemblies described herein when coupling an end effector assembly 660 to a surgical device and/or a loading device, like the surgical devices 100, 100', 400 and the loading devices 1000, 1000', 1400.

As shown in FIG. 15, the end effector assembly 560 can include an end effector 580 disposed at a first end 560d and an attachment or receiving sleeve 562 disposed at a second end 560p. The end effector 580 in the illustrated embodiment includes opposed jaws 582, 584, although any type of end effector provided for herein or otherwise known to skilled in the art can be used (e.g., hooks, knives, snares, monopolar jaws, bipolar jaws, etc.). The attachment arm 562 includes a chamber 564 formed in a terminal end 562t of the arm 562, which is also the terminal end 560t of the end effector assembly 560, and the chamber 564 is configured to receive shaft(s) from a surgical instrument to couple the end effector assembly 560 to the surgical instrument, e.g., the device 100. The chamber 564 includes an opening that is defined by an inner wall 566 of the attachment arm 562.

One or more mating or coupling features can be provided in the chamber 564, including but not limited to male-female mating features, snap-fit configurations, interference-fit configurations, or any number of ways by which two components can be coupled. As shown in FIG. 16, opposed slots 567 (only one is visible) can be formed in a surface of the inner wall 566.

Figure 17A:
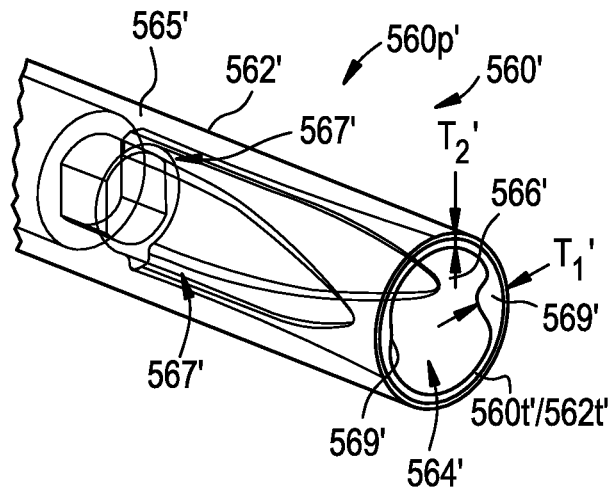
FIG. 17A is a perspective, partially transparent view of one end of another exemplary embodiment of an end effector assembly.
Figure 17B:
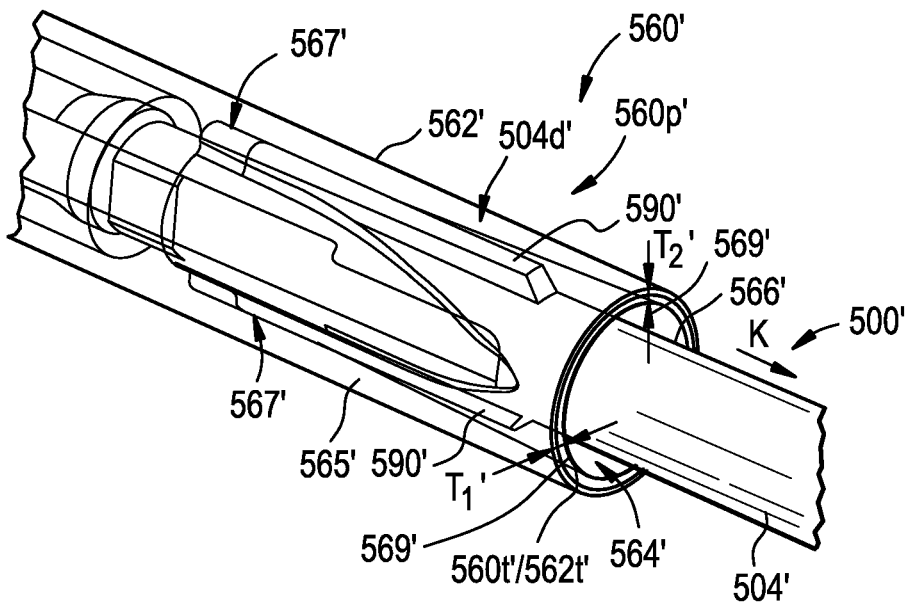
FIG. 17B is the perspective, partially transparent view of the end effector assembly of FIG. 17A, the assembly having a shaft of a surgical device disposed therein.
Figure 18A:
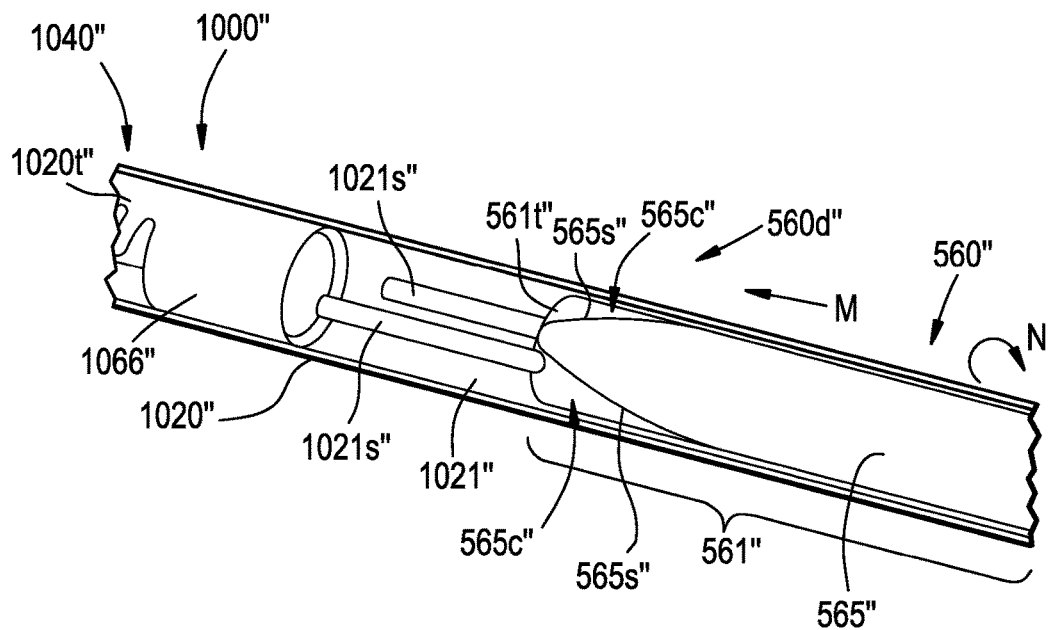
FIG. 18A is a perspective, partially transparent view of a distal end of one exemplary embodiment of a loading device having an end effector assembly at least partially disposed in the loading device such that the end effector assembly is in an unlocked configuration.
Figure 18B:
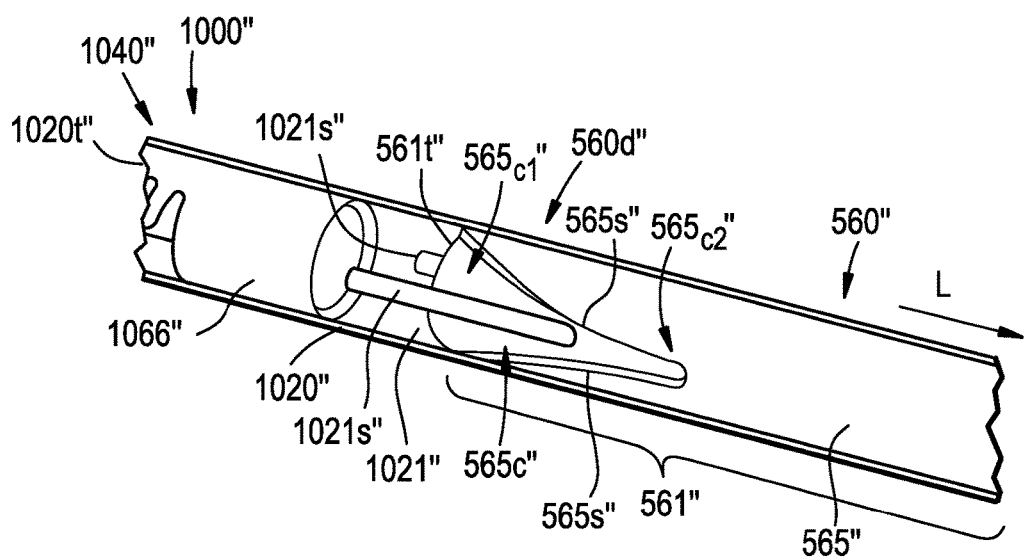
FIG. 18B is a perspective, partially transparent view of the distal end of the loading device of FIG. 18A in which the end effector assembly is more fully disposed in the loading device as the end effector assembly is advanced towards, or away from, a locked configuration.

An alternative embodiment of an end effector assembly 560' is shown in FIG. 17A to better illustrate opposed slots 567' and other features described below. The assembly 560' includes an attachment arm or receiving sleeve 562', a chamber 564' formed in a terminal end 562t' of the sleeve 562', which is also a terminal end 560t' of the end effector assembly 560', and an inner wall 566' that defines an opening of the chamber 564'. The slots 567, 567' can be sized, shaped, and otherwise configured to be complementary to one or more mating elements or coupling features located on a shaft of a surgical instrument. For example, with respect to the end effector assembly 567' of FIG. 17A, as depicted in FIG. 17B, opposed keyed features or splines 590' can be formed on a distal end 504d' of an outer shaft 504' of a surgical instrument 500'. In the illustrated embodiment the splines 590' are rectangular cuboids having a substantially square or rectangular cross-section, and thus the complementary slots 567' have a rectangular shape that is complementary to the rectangular cuboid shape of the splines 590' with a cross-section that has a substantially square or rectangular shape. A width of the slots 567' can be similar in size to the width of the opposed keyed features 590' so they can be coupled together to form a secure connection between the end effector assembly 560' and the shaft 504'. The secure connection can be maintained during use of the end effector (nor shown in FIGS. 17A and 17B) in conjunction with the surgical instrument 500', and it also can be broken to de-couple the end effector assembly 560' from the surgical instrument 500' when a coupled configuration is no longer desired or necessary. The process for de-coupling the end effector assembly 560, 560' from the surgical instrument 500, 500' will depend on the configuration of the mating features, but in the illustrated embodiment FIGS. 17A and 17B, a sufficient force supplied in a direction K can de-couple the end effector assembly 560' from the outer shaft 504' of the surgical instrument 500'.

Although in the illustrated embodiment the splines 590' and complementary slots 567' have a shape that is described as a rectangular cuboid or rectangular shape with a substantially square or rectangular cross-section, a person skilled in the art will recognize a wide variety of geometries, shapes, and configurations that can be used to couple the end effector assembly 560' to the surgical instrument 500'. Likewise, although in the illustrated embodiment two slots 567' and two splines 590' are shown, any number of slots and splines, or other types of mating or coupling features, can be used.

While the ability to couple an end effector assembly to the outer shaft of the surgical device is helpful, it can be difficult to align the two components to insure they can be coupled together. As shown in FIGS. 16 and 17A, however, the receiving sleeve 562, 562' of the end effector assembly 560, 560' can be configured to assist in directing a shaft of a surgical device towards a portion of the end effector assembly 560, 560' configured to couple with the shaft, e.g., the slots 567, 567' in the illustrated embodiments. In the illustrated embodiments, the inner wall or surface 566, 566' includes a self-clocking or self-aligning feature or configuration for this purpose. More particularly, the inner wall or surface 566, 566' has a curved configuration such that the surface 566, 566' serves to funnel a shaft (e.g., the shaft 504') towards the slots 567, 567' as the shaft is inserted from the terminal end 562t, 562t' towards the end effector 580 (not shown in FIG. 17A) disposed at the other end 560d (not shown in FIG. 17A) of the end effector assembly 560, 560'.

While a person having skill in the art will recognize a plethora of configurations, curves, undulations, and the like that can be formed in and/or on the inner surface 566, 566' to achieve the disclosed capability of better directing a shaft of a surgical instrument towards the mating features of the end effector assembly (e.g., slots 567, 567'), in the illustrated embodiment a pair of opposed apexes 569, 569' are formed as part of the inner surface 566, 566'. The opposed apexes 569, 569' are disposed approximately 90 degrees around a circumference of the chamber 564, 564' from a location of the opposed slots 567, 567', and the portion of the inner surface 566, 566' extending from the apexes 569, 569' and circumferentially towards the slots 567, 567' can thus funnel towards the slots 567, 567'. As shown, the curved configuration from the apexes 569, 569' towards the slots 567, 567' creates one continuous inner surface extending between the apexes 569, 569' and the slots 567, 567', although in other configurations the inner surface 566, 566' does not necessarily have to be a single continuous surface. As a result of this configuration, as a shaft is inserted into the receiving sleeve 562, 562', the end effector assembly 560, 560' rotates with respect to the shaft, into a proper position so that the keyed features 590' (not shown in FIG. 16) can mate with the slots 567, 567' and form a secure connection therebetween. While the inner surface 566, 566' can have a variety of shapes, sizes, and configurations, in some exemplary embodiments, a thickness $T_1$, $T_1'$ of the inner wall 566, 566' approximately at the terminal end 562t, 562t' from an inwardly-most extended portion of the apex 569, 569' to an outer wall 565, 565' can be approximately in the range of about 1 millimeter to about 5 millimeters, and in one embodiment it is about 3 millimeters, while a thickness $T_2$, $T_2'$ of the inner wall 566, 566' at the terminal end 562t, 562t' approximately at a thinnest portion of the receiving sleeve 562, 562', e.g., approximately 90 degrees circumferentially from the apexes 569, 569', can be approximately in the range of about 0.5 millimeters to about 3 millimeters, and in one embodiment it is about 1 millimeter.

In some embodiments, such as the end effector assembly 560 shown in FIGS. 15 and 16, similar self-clocking of self-alignment features, as well as coupling features, can be formed on the outer surface 565 of the end effector assembly 560. In the illustrated embodiment, opposed channels 565c formed in the outer surface 565 of the receiving sleeve 562 can serve the purpose of both self-clocking and coupling the end effector assembly 560 with a surgical instrument or loading device. As shown, the channels 565c are disposed proximate to the terminal end 562t of the attachment sleeve 562. A first, receiving terminal end $565c_1$ of the channel 565c, disposed proximate to the terminal end 562t, has a width that is greater than a width of a second terminal end $565c_2$, which is disposed closer to the end effector 580 than the first terminal end $565c_1$ is disposed. Similar to the slots 567, the width and thickness of the channel 565c at the second terminal end $565c_2$ can be complementary to a mating feature of the surgical instrument so the two can be coupled together for subsequent operation of the end effector 580 by the surgical instrument.

Although complementary mating features of a surgical instrument are not illustrated as being part of the surgical instrument 100, a person skilled in the art will easily be able to determine a complementary shape that can be used in conjunction with coupling the end effector assembly 560 to a surgical instrument by way of the channels 565c. For example, an inner wall of an outer shaft of a surgical instrument can include keyed or mating features having a rectangular cuboid shape for being secured within the second terminal end $565c_2$ of the channel 565. Notably, while the illustrated embodiment of FIGS. 15 and 16 illustrate coupling and self-clocking of self-alignment features on both outer and inner surfaces 565, 566 of the receiving sleeve 562, other embodiments can include just one of these two configurations, or similar configurations derivable from the present disclosure, to secure the end effector assembly to a surgical instrument. The mating and self-clocking or self-alignment features formed on the inner and outer surfaces 566, 565 can be used simultaneously, or individually, using the many different configurations provided for herein or otherwise derivable therefrom.

Alternatively, or additionally, the mating and/or self-clocking or self-alignment features provided for as part of the receiving sleeve 562, 562' can also be provided for as part of the opposite end of the end effector assembly 560, 560', and used in conjunction with coupling an end effector assembly 560, 560' to a loading device, e.g., device 1000. FIGS. 18A and 18B illustrate one, non-limiting example of how channels 565c" formed on an outer surface 565" of an end effector end 560d" of an end effector assembly 560" can be used to removably couple the end effector assembly 560" to a loading device 1000". FIG. 18A illustrates the end effector assembly 560" being disposed in an unlocked configuration with respect to the loading device 1000", while FIG. 18B illustrates the end effector assembly 560" being disposed closer to a locked configuration with respect to the loading device 1000". As shown, opposed channels 565c" are formed in an outer surface 565" of an attachment sleeve 561" that is disposed over and/or around an end effector (not shown) at the end effector end 560d" of the end effector assembly 560". As described herein, the sleeve 561" can be used to both couple the end effector assembly 560" to the loading device 1000", and to serve as a shield for the end effector itself, thus protecting an outside environment, e.g., tissue, from accidental and/or incidental contact with the end effector, e.g., jaws, a cutting device, etc. The sleeve 561" can be removed prior to using the surgical device in a surgical procedure.

The channels 565c" formed in the sleeve 561" can have a configuration similar to the channels 562c formed in the outer surface 565 of the attachment sleeve 562. A width is greater at first terminal ends $565c_1$" of the channels 565c", proximate to a terminal end 561t" of the attachment sleeve 561", than at respective second terminal ends $565c_2$" of the channels 565c". Further, the second terminal ends $565c_2$" can each be configured to receive respective splines 1021s" formed on an inner surface 1021" of a delivery chamber 1020" of a loading device 1000", the splines 1021s" having a complementary shape for being received by the respective second terminal ends $565c_2$" of the channels 565c". As the end effector assembly 560" is moved toward the loading device 1000" in a direction M, i.e., towards the splines 1021s" and tube 1066" of the loading device 1000", the splines 1021s" can contact surfaces 565s" of the channels 565c" that define the channels 565c" and cause the end effector assembly 560" to rotate with respect to the loading device 1000", i.e., in a direction N, as shown between FIGS. 18A and 18B. The connection can be secured by engaging the splines 1021s" in the second terminal ends $565c_2$" of the channels 565c", thus forming a locked configuration. A surgical instrument can then be coupled to the opposite end (not shown) of the end effector assembly 560" using techniques provided for herein, derivable therefrom, or otherwise known to those skilled in the art. A force in a direction L can be supplied once the surgical instrument is coupled to the end effector assembly 560" that is sufficient to de-couple the splines 1021s" from the second terminal ends $565c_2$" of the channels, 565c". The sleeve 561" can then be removed to expose the end effector, thereby allowing the end effector to be operated by the surgical instrument.

In other embodiments, the attachment sleeve 561" can actually be an extension of the end effector, and thus disposed even further distally along the end effector assembly 560" than the end effector is located (i.e., in the embodiment of FIG. 18B, even closer to the tube 1066" than the end effector is described as being located with respect to the figure). Such a configuration may be more suitable for using features associated with an inner surface of the attachment sleeve 561" for purposes of coupling and self-clocking or self-aligning, although some end effectors may be configured such that inner surface features on an attachment sleeve can be used in conjunction with the sleeve being disposed around the end effector. In still other embodiments, features for coupling the end effector assembly to the loading device can be formed directly on the end effector. For example, the outer channels 565c formed in the surface 565 of the attachment sleeve 561 can be formed in outer surfaces of jaws of an end effector.

In still further embodiments, it can be an end of the end effector assembly (e.g., the end 560p, 560p' of the end effector assembly 560, 560') that includes a receiving sleeve (e.g., the receiving sleeve 562, 562') that is disposed in the loading device with the end effector (e.g., the end effector 580, not shown in the embodiment of FIGS. 17A and 17B) being located proximate to a terminal end of the receiving sleeve (e.g., the terminal end 562t, 562t' of the receiving sleeve 562, 562'). As a result, the coupling features associated with the receiving sleeve can be used in conjunction with coupling the end effector assembly to a loading device. In such a configuration, the loading device can have a configuration that allows a surgical instrument to be inserted into the receiving sleeve to couple the surgical instrument to the end effector assembly. For example, a pivot point can be formed in a loading device at a pivot joint, such as the pivot joint 1040" shown in FIGS. 18A and 18B, such that the delivery chamber 1020" pivots with respect to the rest of the loading device 1000" at the pivot joint 1040". Pivoting at the pivot joint 1040" can subsequently expose a terminal end 1020t" of the delivery chamber 1020", which can include an opening (not shown) formed in the tube 1066" through which a shaft of a surgical instrument can be inserted to couple the end effector assembly to the surgical instrument for subsequent use.

A person skilled in the art will recognize many other configurations that can be used between loading devices, end effector assemblies, and surgical devices to take advantage of the self-clocking and self-alignment features provided for herein without departing from the spirit of the present disclosure. Further, to the extent the disclosures of FIGS. 14-18B are described as a self-clocking or self-alignment feature being unitary with a mating feature (e.g., the inner surface 566' configuration in conjunction with the slots 567'), a person skilled in the art will recognize that these two features can be separate from each other. Still further, any number of sizes, shapes, and configurations of self-clocking features, and mating features for that matter, can be used without departing from the spirit of the present disclosure. A person skilled in the art, in view of the present disclosures, can easily adapt a size, shape, and/or configuration of one or more self-clocking features to facilitate easier coupling between the end effector assembly and either or both of a surgical instrument and a loading device.

Figure 19:
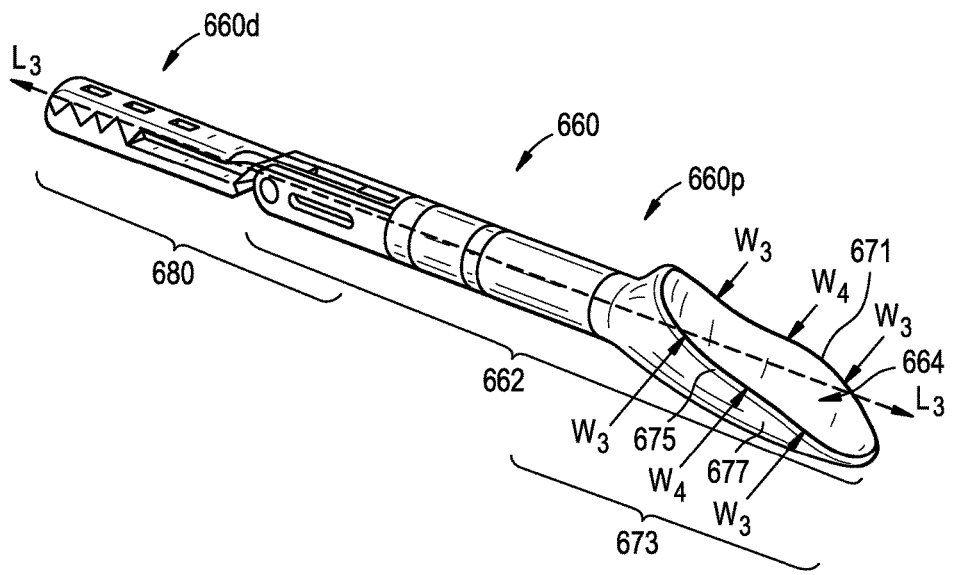
FIG. 19 is a perspective view of still another exemplary embodiment of an end effector assembly.
Figure 20:
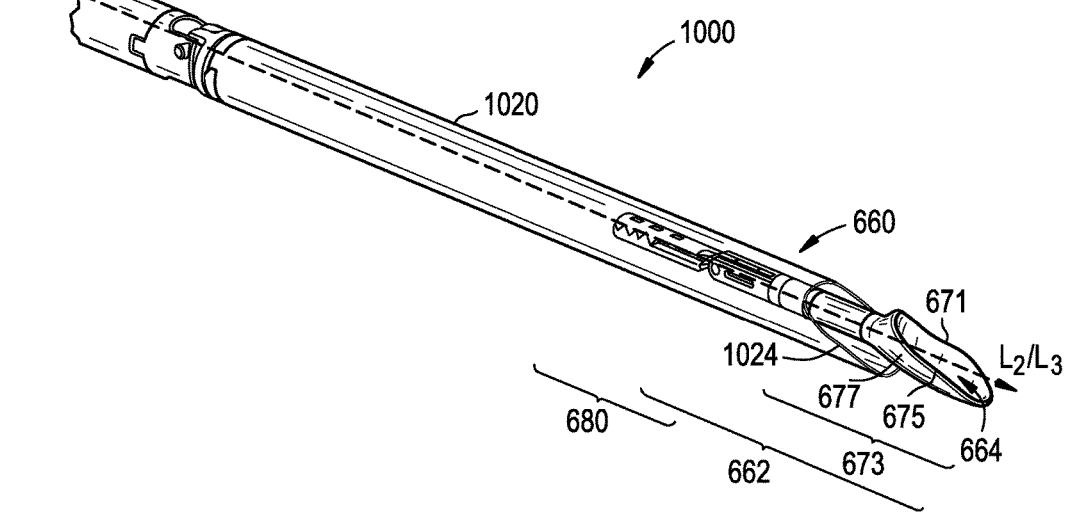
FIG. 20 is a perspective, partially transparent view of the end effector assembly of FIG. 19 disposed in the loading device of FIG. 10A.

FIGS. 19 and 20 provide for another exemplary embodiment of an end effector assembly 660. As shown, a first end 660*d* of the end effector assembly 660 includes an end effector 680, and a second, opposite end 660*p* includes an attachment arm or receiving sleeve 662 configured to provide an improved three-dimensional surface to make it easier to mate the end effector assembly 660 to a shaft of a surgical instrument in vivo. A terminal end surface 671 of the attachment arm 662 includes an opening 664 formed therein, the opening 664 being defined by the terminal end surface 671 (sometimes referred to as a distal-most outer wall) and an inner surface 666 of the attachment arm 662. As shown, a first portion 671*a* of the terminal end 660*d* extends further way from the first end 660*d* along a longitudinal axis $L_3$ of the end effector assembly 660 than a second portion 671*b* of the terminal end surface 671 extends away from the first end 660*d* along the longitudinal axis $L_3$. As illustrated in FIG. 20, in which the longitudinal axes $L_2$ and $L_3$ are substantially aligned, the shape of the opening 664 defined by the terminal end surface 671, based on the configurations of the first and second portions 671*a*, 671*b*, can be similar to the shape of the terminal end surface 1024 of the delivery chamber 1020 of the loading device 1000. In other words, the shapes of the two surfaces 1024 and 671, or at least portions thereof, can substantially mirror each other. This can help a user better identify the location of the end effector assembly 660 with respect to the loading device 1000 when trying to couple a shaft of a surgical instrument to the end effector assembly 660, and keep the components better aligned with respect to each other. This is because having one portion 671*b* of the terminal end surface 671 positioned deeper than another portion 671*a* of the terminal end surface 671 provides cues to the user about the location and alignment of the end effector assembly 660 with respect to the loading device 1000 and the surgical instrument to which the end effector assembly 660 is going to be coupled.

Any number of three-dimensional shapes can be used to form the terminal end surface 671 of the attachment arm 662, but in the illustrated embodiment, a shape of the terminal end surface 671 is approximately trough or scallop-shaped, just as the terminal end surface 1024 of the loading device 1000 is approximately trough or scallop-shaped. More particularly, a width of the first portion 671*a* and a width of the second portion 671*b* is greater than a width of an intermediate portion 671*i* disposed between the first and second portions 671*a*, 671*b*. In some exemplary embodiments, the first portion 671*a* is approximately in the range of about 2 millimeters to about 20 millimeters longer than the second portion 671*b* at their distal-most ends, and in one exemplary embodiment that difference in length is about 5 millimeters. Further, in some exemplary embodiments, a width $w_3$ (labeled in FIG. 19) of the first and second portions 671*a*, 671*b* is approximately in the range of about 2 millimeters to about 10 millimeters, while a width $w_4$ (labeled in FIG. 19) of the intermediate portion 671*i* is approximately in the range of about 1 millimeter to about 8 millimeters, and in one exemplary embodiment the widths $w_3$ of the first and second portions 671*a*, 671*b* is about 5 millimeters and the width $w_4$ of the intermediate portion 671*i* is about 3 millimeters. In some embodiments, the widths $w_3$ of the first and second portions 671*a*, 671*b* can be different.

The portion of the attachment arm 662 that provides the three-dimensional shape, sometimes referred to as an end sleeve 673, can be associated with the rest of the end effector assembly 660 in a variety of ways. In some instances, the end sleeve 673 can be formed as part of the rest of the attachment arm 662 such that the three-dimensionally shaped portion is of a unitary construction with the rest of the attachment arm 662. In other instances, the end sleeve 673 can be an additional structure attached to the end of a typical end effector assembly, such as other end effector assemblies disclosed herein or otherwise known to those skilled in the art. For example, the end sleeve 673 can be an elastic conical end sleeve that is coupled to an attachment arm of an end effector assembly. In some instances, an attached end sleeve 673 can be a foaming flexing isoprene. Still further, in some embodiments, a flexible skirt 675 can be provided as part of the proximal surface 677 to provide additional feedback about the location of the end effector assembly 660, and provide enhanced visualization of the end 660*p* of the end effector assembly 660. The skirt 675 can further increase the size of a landing zone to make aligning a shaft of an instrument with the end effector assembly 660 easier. A person skilled in the art will recognize many other ways this three-dimensional end sleeve 673 can be provided, and a variety of other materials that can be used to form it, including but not limited thermoplastic elastomers.

Additionally, while in the embodiments provided for herein generally discuss the end sleeve 673 having an opening 664 for a shaft to be inserted therethrough to couple a surgical instrument to the end effector assembly 660, an opening is not necessary. The configuration of the end sleeve 673, and/or an attachment sleeve as provided for in this embodiment and previously discussed embodiments, can be any configuration that facilitates coupling with a surgical instrument, and thus the configuration can depend, at least in part, on the configuration of the surgical instrument to which it is to be attached, the type of procedure being performed, and the preferences of the user. Accordingly, in some embodiments there may be no opening 664 and the terminal end surface 671 may be a closed surface with attachment features for the end effector assembly 660 being associated with an outer surface of the end effector assembly 660 and/or the surgical instrument being configured to couple to the end effector assembly 660 directly without specially adapted features associated with the end effector assembly 660 to facilitate engagement between the two. By way of non-limiting example, in some embodiments the end sleeve 673 can have no opening 664, and thus the entire terminal end surface 671 (which as described in this embodiment would generally include an area previously described as the opening 664) can provide feedback to a user about the location and alignment of the end effector assembly 660 with respect to the loading device 1000 and a surgical instrument to which the end effector assembly 660 is to be attached. Instead, one or more coupling features, such as channels formed on an outer surface like the channels 565*c* described above, can be provided for on the outer surface of the end effector assembly 660, and/or the surgical instrument can include features that allow the end effector assembly 660 to be removably coupled to the instrument.

While some of the components are described herein as having particular dimensions and materials, a person skilled in the art will recognize typical dimensions and materials used for making surgical instruments and end effector assemblies. It is thus not necessary to provide specific dimensions or materials for each of the described components. To the extent some dimensions or materials are provided for herein with respect to particular components, those dimensions and materials were not necessarily known to those skilled in the art as suitable for use with the present disclosure prior to the existence of the present disclosure. By way of non-limiting examples, components of surgical instruments, including the shafts, end effector assemblies, and the loading device can be made from surgical grade stainless steel (e.g., 17-4), other 300 and 400 series stainless steels, titanium, and aluminum, and components of surgical instruments and loading devices that are designed to be gripped or house other components, such as the housing or handle portion, can be made from a polymer (e.g., polycarbonate). A person skilled in the art will recognize that internal components of items like surgical instruments and loading devices may include motors, controllers, levers, etc., which can be made from various materials typically used to form such components.

Further, a person skilled in the art will recognize that the methods of using the various surgical devices, end effector assemblies, loading devices, and other related components provided for herein are understood or derivable from the description of the devices, assemblies, and related components themselves. Accordingly, to the extent the present disclosure does not provide every detail about how one component works with respect to another, a person skilled in the art will be able to make those determinations in view of the present disclosures and the person's baseline knowledge. In some instances, some exemplary methods associated with using certain components of certain embodiments, or at least portions of exemplary methods, are described herein. For example, some exemplary methods of using the lock spring 168 in FIGS. 7A-7C are described above, as are some exemplary methods of removing and replacing shafts 104, 140, and 130 with respect to the housing 102. Nevertheless, by way of non-limiting example, to the extent there are not explicit disclosures about each and every possible interaction of using removable and replaceable shafts like those in FIGS. 2-3F with respect to one or more end effector assemblies, one or more housings, and/or related components, a person skilled in the art will be able to determine from the present disclosures how to operate and switch out the shafts, end effector assemblies, housings, and related components as desired in view of the present disclosures. Which end effectors assemblies, shafts, and housings are used will depend, at least in part, on the type of procedure being performed, the demographics of the patient, and the other components being used with the devices and related components, among other factors.

The above paragraph notwithstanding, in one exemplary method of using at least some of the features discussed above, a surgical method involving the operation of one or more end effectors at a surgical site is described below. After forming a first surgical opening for use with a surgical device and a second surgical opening for use with a loading device, and inserting the appropriate instrument through the opening to form the necessary seals, e.g., a trocar, a surgical device 100 can be inserted through the first opening (not shown) and a loading device 1000 can be inserted through the second opening (not shown), as illustrated by FIG. 8. Prior to inserting the surgical device 100 into the first opening, the desired shaft(s) 104, 140, 130 (130 not being shown in FIG. 8) can be associated with the housing 102 using techniques described above with respect to FIGS. 2-3F, or using other techniques known to those skilled in the art. Likewise, prior to inserting the loading device 1000 into the second opening, an end effector assembly (not shown in FIG. 8) can be predisposed in a delivery chamber 1020 of the loading device 1000. In some of the embodiments provided for herein, the end effector assembly is held within the delivery chamber 1020 by magnets (FIGS. 11A-13C) or by features such as complementary splines and slots (FIGS. 18A-18B), although other techniques for holding an end effector assembly in a loading device either discussed herein or otherwise known to those skilled in the art can also be used. Alternatively, the end effector assembly can be associated with the loading device 1000 after the loading device 1000 is disposed in the second opening. For example, the loading device 1000 can have a passage extending from a handle portion 1002 located at a proximal end 1000p of the device 1000 to the distal chamber 1020 located at a distal end 1000d of the device 1000 to allow end effectors to be exchanged multiple times during the course of a procedure.

The loading device 1000 can be operated to rotate the delivery chamber 1020 with respect to the longitudinal axis $L_2$ thereof, thereby presenting the delivery chamber 1020, and its contents (e.g., the end effector assembly disposed therein) in a manner that is conducive for attachment to the surgical device 100 (not shown in FIG. 20). An articulated, loading configuration of a delivery chamber 1020' being angled at an angle γ' with respect to a longitudinal axis $L_2'$ is provided in FIGS. 11A-11B. The surgical device can then be advanced towards the delivery chamber 1020 to begin facilitating the attachment of the end effector assembly to the surgical device. Many different features for facilitating this interaction are provided for herein, and any combination of these features, or any one of these features on their own, can be used in conjunction with the method. For example the magnetic interactions provided for in FIGS. 13A-13C can be used in conjunction with coupling the end effector assembly with the surgical device.

Alternatively, or additionally, the mating features and/or alignment features provided for in FIGS. 15-17B and/or FIGS. 19-20 can be used in conjunction with coupling the end effector assembly with a surgical device. Thus, the method can involve contacting a distal end 104d of the shaft 104 of the surgical device 100 with the terminal end surface 1024 of the delivery chamber 1020 that is shaped like the one illustrated in FIGS. 8-11B, 14, and 20, and/or contacting the distal end 104d with the terminal end surface 671 of an end effector assembly 660 that is shaped like the one illustrated in FIGS. 19-20 to identify a position of the end effector assembly. The shaft 104 would be able to recognize the first portions 1024a and/or 671a extending further away from the opposite ends 1020p and/or 660d along the longitudinal axis $L_2$ and/or $L_3$ than the second portion 1024b and/or 671b extends away from the opposite ends 1020p and/or 660d along the longitudinal axis $L_2$ and/or $L_3$, thereby promoting identification of the position of the delivery chamber 1020 and/or the end effector assembly 660. Further, if an inner surface of the end effector assembly was constructed similar to the inner surfaces 566, 566' of the end effector assemblies 560, 560' of FIGS. 15-17B, the shaft 104 can be aligned and directed towards the mating feature(s) of the end effector assemblies 560, 560'), e.g., the slots 567, 567' that are complementary in shape to a spline formed on the shaft 104, by being guided along the inner surfaces 566, 566' that form a funnel from respective apexes 569, 569' towards the mating feature(s). A secure attachment can then be made between the slots 567, 567' and splines. In some embodiments, the secure attachment can be confirmed by incorporating a lock spring like the lock spring 168 illustrated in FIGS. 7A-7C with the end effector assembly.

After a secure attachment has been made, the end effector assembly 660 and surgical device 100 can be removed from the loading device 1000 and operated. Subsequently, the end effector assembly 660 can be detached from the surgical device 100 using techniques known to those skilled in the art and/or derivable from the present disclosures, including those described or derivable from the disclosures associated with FIGS. 1-6B, and the end effector assembly 660 can be passed back into the loading device 1000 and removed from the surgical site. Other methods for removing an end effector from a surgical site can also be employed without departing from the spirit of the present disclosure. Further, other end effector assemblies can be introduced and coupled to the surgical device 100 as desired. Upon completion of the procedure, the surgical device 100 and loading device 1000 can be removed from the surgical site and cleaned and sterilized as desired. Any component that is detachable from another, by way of non-limiting examples, the end effector assembly from the shaft 104 and the shafts 104, 140, 130 from the housing 102, can be cleaned and sterilized. These components can be reused if desired.

A person skilled in the art will appreciate that the present invention has application in conventional endoscopic and open surgical instrumentation as well application in robotic-assisted surgery.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the devices described herein will be processed before surgery. First, a new or used instrument is obtained and if necessary cleaned. The instrument can then be sterilized. In one sterilization technique, the instrument is placed in a closed and sealed container, such as a plastic or TYVEK® bag. The container and its contents are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam.

One skilled in the art will appreciate further features and advantages of the invention based on the above-described embodiments. Accordingly, the invention is not to be limited by what has been particularly shown and described, except as indicated by the appended claims. Further, any feature from one embodiment can be readily incorporated by a person having ordinary skill in the art to other embodiments in view of the present disclosures. This includes, but is not limited to adapting the end sleeve 673 of FIGS. 19 and 20, the self-clocking and self-alignment features of FIGS. 14-18B, the mating features of FIGS. 11A-13C, the delivery chamber terminal end 1024 shape and configuration of FIGS. 8-10B (and also illustrated in FIGS. 11A, 11B, 14, and 20), the lock spring 168 of FIGS. 7A-7C, and the modularity of end effectors, shafts 104, 140, 130, and the housing 102 of FIGS. 1A-6B for use in any of the other embodiments provided for herein, derivable therefrom, or otherwise known to those skilled in the art. Likewise, a person skilled in the art will understand how to make any necessary adaptations to use the various features provided for herein with a variety of types of end effectors, i.e., not just jaws. Still further, a person skilled in the art will understand how to incorporate features described with respect to one component of a system (e.g., an end effector assembly, a surgical device, and a loading device) into another component of a system. Accordingly, to the extent a feature is described as being associated with an end effector assembly, a surgical device, or a loading device, such feature can also be included as a feature in another of an end effector assembly, a surgical device, or a loading device. All publications and references cited herein are expressly incorporated herein by reference in their entirety.

What is claimed is:

1. A surgical device comprising: an elongate shaft with a magnetic feature disposed on a distal portion thereof; and an end effector assembly that is configured to couple to the elongate shaft, the end effector assembly comprising: an end effector disposed at a first distal end, an attachment arm disposed at a second, opposite proximal end, the attachment arm having a terminal end surface defining an opening for receiving an the elongate shaft configured to be coupled to the end effector assembly, and a first magnet disposed at a proximal portion of the end effector assembly, the first magnet having a polarity that is configured to repel a polarity of the magnetic feature when the elongate shaft is inserted into the attachment arm such that the end effector assembly at least partially rotates relative to the elongate shaft to self-align the end effector assembly with the elongate shaft.

2. The surgical device of claim 1, wherein the attachment arm further comprises an elongate shaft extending between the terminal end surface and the end effector, the end effector being operatively coupled to an end of the elongate shaft that is opposed to the terminal end surface.

3. The surgical device of claim 1, wherein the end effector comprises a jaw assembly.

4. The surgical device of claim 1, wherein a second magnet is disposed at a distal portion of the end effector assembly, wherein the second magnet has a polarity that is configured to attract the polarity of the magnetic feature when the elongate shaft is inserted into the attachment arm.

5. The surgical device of claim 1, wherein the end effector assembly is configured to rotate relative to the elongate shaft so as to couple the magnetic feature with the end effector assembly.

6. The surgical device of claim 1, wherein the end effector assembly includes a radially inward extending wall that is configured to engage the magnetic feature such that once the elongate shaft is coupled to the end effector assembly, further advancement of the elongate shaft into the end effector assembly is prevented.

7. A surgical device comprising: a surgical instrument having an elongate shaft with a magnet disposed on a distal portion thereof; an end effector assembly that is configured to couple to the surgical instrument such that, when the end effector assembly is being coupled to the surgical instrument, the end effector assembly magnetically repels a polarity of the magnet of the elongate shaft such that the end effector assembly at least partially rotates relative to the surgical instrument to self-align the end effector assembly with the surgical instrument; and a loading device having a delivery chamber that is configured to house at least a portion of the end effector assembly.

8. The surgical device of claim 7, wherein the elongate shaft has opposed deflectable arms, and the magnet is coupled to one of the opposed deflectable arms.

9. The surgical device of claim 7, wherein the delivery chamber has a magnet disposed in a proximal portion thereof, and wherein the magnet is configured to attract the end effector to maintain the portion of the end effector assembly within the delivery chamber.

10. The surgical device of claim 7, wherein a first magnet is disposed at a proximal portion of the end effector assembly, and wherein the magnet of the end effector assembly has a polarity that is configured to repel the polarity of the magnet of the elongate shaft when the elongate shaft is inserted into the end effector assembly.

11. The surgical device of claim 10, wherein a second magnet is disposed at a distal portion of the end effector assembly, and wherein the magnet has a polarity that is configured to attract the polarity of the magnet of the elongate shaft when the elongate shaft is inserted into the end effector assembly.

12. The surgical device of claim 7, wherein the end effector assembly is configured to rotate relative to the surgical instrument so as to couple the magnet of the elongate shaft with the end effector assembly.

13. The surgical device of claim 7, wherein the end effector assembly has a radially inward extending wall that is configured to engage the magnet of the elongate shaft such that once the surgical instrument is coupled to the end effector assembly, further advancement of the surgical instrument into the end effector assembly is prevented.

* * * * *